United States Patent [19]

Vande Woude et al.

[11] Patent Number: 5,645,988

[45] Date of Patent: Jul. 8, 1997

[54] METHODS OF IDENTIFYING DRUGS WITH SELECTIVE EFFECTS AGAINST CANCER CELLS

[75] Inventors: George F. Vande Woude, Berryville, Va.; Han-Mo Koo, Gaithersburg; Anne Monks, Clarksburg, both of Md.

[73] Assignee: The United States of America as represented by the Department of Health and Human Services, Washington, D.C.

[21] Appl. No.: 260,515

[22] Filed: Jun. 15, 1994

Related U.S. Application Data

[63] Continuation-in-part of Ser. No. 169,962, Dec. 20, 1993, which is a continuation of Ser. No. 880,525, May 8, 1992, abandoned, which is a continuation-in-part of Ser. No. 696,923, May 8, 1991, abandoned.

[51] Int. Cl.$^6$ ................................................. C12Q 1/68
[52] U.S. Cl. ................................................. 435/6; 435/32
[58] Field of Search ............................ 435/5, 6, 172.3, 435/240.2, 240.21, 32

[56] References Cited

U.S. PATENT DOCUMENTS

| | | | |
|---|---|---|---|
| 4,357,352 | 11/1982 | Swallow | 424/330 |
| 4,885,238 | 12/1989 | Reddel et al. | 435/29 |
| 5,034,544 | 7/1991 | Elliott | 549/435 |
| 5,248,671 | 9/1993 | Smith | 514/44 |

FOREIGN PATENT DOCUMENTS

WO 94/28127  12/1994  WIPO.

OTHER PUBLICATIONS

Bai et al., "Halichondrin B and Homohalichondrin B, Marine Natural Products Binding in the Vinca Domain of Tubulin", *J. Biolog. Chem.*, 266, 15882–15889 (1991).
Barbacid, "ras Genes", *Ann. Rev. Biochem.*, 56, 779–837 (1987).
Bos, "ras Oncogenes in Human Cancer: A Review", *Cancer Research*, 49, 4682–4689, (1989).
Monks et al., "Feasibility of a High–Flux Anticancer Drug Screen Using a Diverse Panel of Cultured Human Tumor Cell Lines", *Journal of the National Cancer Institute*, 83:11, 757–766 (1991).
Paull et al., "Display and Analysis of Patterns of Differential Activity of Drugs Against Human Tumor Cell Lines: Development of Mean Graph and Compare Algorithm", *Journal of the National Cancer Institute*, 81:14, 1088–1092 (1989).
Paull et al., "Identification of Novel Antimitotic Agents Acting at the Tubulin Level by Computer–assisted Evaluation of Differential Cytotoxicity Data", *Cancer Research*, 52, 3892–3900 (1992).
Perkins et al., "Principles of Molecular Cell Biology of Cancer: Oncogenes", In: *Cancer: Principles & Practice of Oncology*, 4th Ed., DeVita, Jr., et al., eds., 35–57 (PA: J.B. Lippincott Co., 1993).
Siegel, "Measures of Correlation and Their Tests of Significance", *Nonparametric Statistics for the Behavioral Sciences*, 195–213 (NY: McGraw–Hill Book Co., 1956).
Skehan et al., "New Colorimetric Cytotoxicity Assay for Anticancer–Drug Screening", *Journal of the National Cancer Institute*, 82:13, 1107–1112 (1990).
Snedecor et al., "Correlation", In: *Statistical Methods*, 7th Ed., 175–193 (Ames, IA: The Iowa State University Press, 1980).
Weinstein et al., "Neural Computing in Cancer Drug Development: Predicting Mechanism of Action", *Science*, 258, 447–451 (1992).
Wu et al., "Multidrug–resistant Phenotype of Disease–oriented Panels of Human Tumor Cell Lines Used for Anticancer Drug Screening", *Cancer Research*, 52, 3029–3034 (1992).
Bos, *Cancer Research*, vol. 49, 1989, pp. 4682–4689.
Alley et al., *Cancer Research*, vol. 48, 1988, pp. 589–601.

*Primary Examiner*—James S. Ketter
*Attorney, Agent, or Firm*—Leydig, Voit & Mayer, Ltd.

[57] ABSTRACT

The present invention involves a method of identifying drugs which selectively inhibit the growth of particular cancer cells, which method comprises: (a) contacting with the drug at least two cancer cells derived from the same type of biological material, wherein the cancer cells differ as to the presence of a particular DNA sequence, (b) measuring the effect of the drug on the growth of the cancer cells, and (c) determining whether there is a correlation between the effect of the drug on the cancer cells and the presence or absence of the DNA sequence in the cancer cells. The present invention further involves the use of such drugs.

19 Claims, 1 Drawing Sheet

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:1:

GCCGCCTGCA GCCCGCGCCC CCCGTGCCCC CGCCCCGCCG CCGGCCCGGC CGCC                54

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:2:

GGCCTGCTGA AAATGACTGA                                                       20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:3:

GTCCTGCACC AGTAATATGC                                                       20

(2) INFORMATION FOR SEQ ID NO:4:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (synthetic)

(ix) FEATURE:
        (C) OTHER INFORMATION: The first 54 nucleotides of the 5
        end comprise the GC clamp.

(xi) SEQUENCE DESCRIPTION: SEQ ID NO:4:

GCCGCCTGCA GCCCGCGCCC CCCGTGCCCC CGCCCCGCCG CCGGCCCGGC CGCCGTCCTG          60

CACCAGTAAT ATGC                                                             74

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:5:

CCAGACTGTG TTTCTCCCTT C                                                     21

(2) INFORMATION FOR SEQ ID NO:6:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (synthetic)

(ix) FEATURE:

(C) OTHER INFORMATION: The first 54 nucleotides of the 5
end comprise the GC clamp.

( x i ) SEQUENCE DESCRIPTION: SEQ ID NO:6:

GCCGCCTGCA GCCCGCGCCC CCCGTGCCCC CGCCCCGCCG CCGGCCCGGC CGCCCCAGAC    60

TGTGTTTCTC CCTTC    75

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

CACAAAGAAA GCCCTCCCCA    20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

GACTGAGTAC AAACTGGTGG    20

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

GGGCCTCACC TCTATGGTG    19

( 2 ) INFORMATION FOR SEQ ID NO:10:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (synthetic)

( i x ) FEATURE:
        ( C ) OTHER INFORMATION: The first 54 nucleotides of the 5
        end comprise the GC clamp.

( x i ) SEQUENCE DESCRIPTION: SEQ ID NO:10:

GCCGCCTGCA GCCCGCGCCC CCCGTGCCCC CGCCCCGCCG CCGGCCCGGC CGCCGGGCCT    60

CACCTCTATG GTG    73

( 2 ) INFORMATION FOR SEQ ID NO:11:

( i ) SEQUENCE CHARACTERISTICS:
        ( A ) LENGTH: 20 base pairs ( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:11:

GGTGAAACCT GTTTGTTGGA                                                        20

( 2 ) INFORMATION FOR SEQ ID NO:12:

( i ) SEQUENCE CHARACTERISTICS:
( A ) LENGTH: 74 base pairs
( B ) TYPE: nucleic acid
( C ) STRANDEDNESS: single
( D ) TOPOLOGY: linear ( i i ) MOLECULE TYPE: DNA (synthetic)

( i x ) FEATURE:
( C ) OTHER INFORMATION: The first 54 nucleotides of the 5
end comprise the GC clamp.

( x i ) SEQUENCE DESCRIPTION: SEQ ID NO:12:

GCCGCCTGCA GCCCGCGCCC CCCGTGCCCC CGCCCCGCCG CCGGCCCGGC CGCCGGTGAA            60

ACCTGTTTGT TGGA                                                              74

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:13:

ATACACAGAG GAAGCCTTCG                                                        20

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:14:

CAGGCCCCTG AGGAGCGATG                                                        20

( 2 ) INFORMATION FOR SEQ ID NO:15:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:15:

TTCGTCCACA AAATGGTTCT                                                        20

( 2 ) INFORMATION FOR SEQ ID NO:16:

( i ) SEQUENCE CHARACTERISTICS:

(A) LENGTH: 74 base pairs
(B) TYPE: nucleic acid
(C) STRANDEDNESS: single
(D) TOPOLOGY: linear (ii) MOLECULE TYPE: DNA (synthetic)

(ix) FEATURE:
(C) OTHER INFORMATION: The first 54 nucleotides of the 5 end comprise the GC clamp.

(xi) SEQUENCE DESCRIPTION: SEQ ID NO:16:

GCCGCCTGCA GCCCGCGCCC CCCGTGCCCC CGCCCGCCG CCGGCCCGGC CGCCTTCGTC    60

CACAAAATGG TTCT    74

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:17:

TCCTGCAGGA TTCCTACCGG    20

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:18:

GGTTCACCTG TACTGGTGGA    20

(2) INFORMATION FOR SEQ ID NO:19:

(i) SEQUENCE CHARACTERISTICS:
(A) LENGTH: 74 base pairs
(B) TYPE: nucleic acid
(C) STRANDEDNESS: single
(D) TOPOLOGY: linear (ii) MOLECULE TYPE: DNA (synthetic)

(ix) FEATURE:
(C) OTHER INFORMATION: The first 54 nucleotides of the 5 end comprise the GC clamp.

(xi) SEQUENCE DESCRIPTION: SEQ ID NO:19:

GCCGCCTGCA GCCCGCGCCC CCCGTGCCCC CGCCCGCCG CCGGCCCGGC CGCCGGTTCA    60

CCTGTACTGG TGGA    74

METHODS OF IDENTIFYING DRUGS WITH SELECTIVE EFFECTS AGAINST CANCER CELLS

CROSS-REFERENCE TO RELATED APPLICATIONS

The present application is a continuation-in-part of co-pending U.S. application Ser. No. 08/169,962 filed Dec. 20, 1993; which is a continuation of U.S. application Ser. No. 07/880,525 filed May 8, 1992, now abandoned; which is a continuation-in-part of U.S. application Ser. No. 07/696,923 filed May 8, 1991, now abandoned.

TECHNICAL FIELD OF THE INVENTION

The present invention concerns a method of identifying drugs which selectively inhibit the growth of particular cancer cells as well as methods of using such drugs.

BACKGROUND OF THE INVENTION

The duplication of genetic information and its partitioning to progeny cells are fundamental to the survival and propagation of all eukaryotes. Many lines of evidence suggest that proto-oncogenes and tumor suppressor genes are part of the hierarchy of genes that regulate these processes. Proto-oncogenes stereotypically are positive regulators of the cell cycle and, when their oncogenic potential is activated (i.e., they become oncogenes), comprise a gain of function in the cell. In contrast, tumor suppressor genes (or recessive oncogenes) are negative regulators, and transformation is promoted through their loss of function (Perkins et al., In: *Cancer: Principles and Practices of Oncology*, 4th ed., DeVita et al., eds., (PA: J. B. Lippincott Co., 1993) 35–57). Many of these transforming genes for which human homologs have been discovered are set forth in Table 1, and the cellular localization of representative oncogenes is depicted in FIG. 1 (Vande Woude et al., In: *Views of Cancer Research*, Fortner et al., eds., (PA: J. B. Lippincott Co., 1990) 128–143; Perkins et al., In: *Cancer: Principles and Practices of Oncology*, 4th ed., DeVita et al., eds., (PA: J. B. Lippincott Co., 1993) 35–57).

TABLE 1

Source and Properties of Oncogenes

| RNA Tumor Virus | Oncogene | Species of Origin | Source | Properties |
| --- | --- | --- | --- | --- |
| Integral Membrane Tyrosine Kinases | | | | |
| Susan McDonough feline sarcoma virus | v-fms | Cat | Sarcoma | From CSF 1 receptor |
| Avian erythroblastosis virus | v-erbB | Chicken | Sarcoma/erythroblastosis | From EGF receptor |
| HZ4 feline sarcoma virus | v-kit | Cat | Sarcoma | |
| UR2 avian sarcoma virus | v-ros | Chicken | Sarcoma | |
| | neu | Rat | Neuroblastoma | |
| | met | Human | MNNG-treated human osteosarcoma cell line | From HGF/SF receptor |
| | trk | Human | Colon carcinoma | From NGF receptor |
| Membrane-Associated Tyrosine Kinases | | | | |
| Rous sarcoma virus | v-src | Chicken | Sarcoma | |
| Yamaguchi-79 sarcoma virus | v-yes | Chicken | Sarcoma | |
| Gardner-Rasheed feline sarcoma virus | v-fgr | Cat | Sarcoma | |
| Fujinami sarcoma virus | v-fps | Chicken | Sarcoma | |
| Snyder-Theilen virus | v-fes | Cat | Sarcoma | |
| Abelson murine leukemia virus | v-abl | Mouse | Leukemia | |
| Hardy Zuckerman 2 feline sarcoma virus | v-abl | Cat | Sarcoma | |
| Serine-Threonine Kinases | | | | |
| Moloney murine sarcoma virus | v-mos | Mouse | Sarcoma | |
| 3611 murine | raf | Mouse | Sarcoma | |
| Growth Factor Families | | | | |
| Simian sarcoma virus | v-sis | Monkey | Glioma/fibrosarcoma | B chain PDGF |
| | int-2 | Mouse | Mammary carcinoma | Member of FGF family |
| | ks3 | Human | Kaposi carcinoma | Member of FGF family |
| | hst | Human | Stomach carcinoma | Member of FGF family |
| Ras Family | | | | |
| Harvey murine sarcoma virus | v-H-ras | Rat | Erythroleukemia | GTP binding/GTPase |
| Kirsten murine sarcoma virus | v-K-ras | Rat | Sarcoma | GTP binding/GTPase |
| | N-ras | Human DNA | Various | GTP binding/GTPase |
| Nuclear Protein Family | | | | |
| Myelocytomatosis-29 virus | v-myc | Chicken | Carcinoma myelocytomatosis | Binds DNA |
| | N-myc | Human | Neuroblastoma | |
| | L-myc | Human | Small cell lung carcinoma | |
| Avian myeloblastosis virus | v-myb | Chicken | Myeloblastosis | Binds DNA |
| FBJ murine sarcoma | v-fos | Mouse | Osteosarcoma | Binds DNA |
| Sloan-Kettering avian sarcoma virus | v-ski | Chicken | Carcinoma | |
| | v-jun | Chicken | | Binds DNA |

TABLE 1-continued

| | | Source and Properties of Oncogenes | | |
|---|---|---|---|---|
| RNA Tumor Virus | Oncogene | Species of Origin | Source | Properties |
| Others | p53 | Mouse/human | Expressed at high levels in transformed cells | Binds SV40 large T/and adenovirus E1B |
| Reticuloendotheliosis virus, strain T | v-rel | Turkey | Lymphatic leukemia | |
| E26 avian leukemia virus | v-ets | Chicken | | |
| Avian erythroblastosis virus | v-erbA | Chicken | Erthroblastosis | Derived from steroid receptor fo triiodothyronine |
| | mas | Human | Mammary carcinoma | Transmembrane protein |
| | int1 | Mouse | Mammary carcinoma | |

While the number of oncogenes discovered continues to increase, the number of families to which they have been assigned has not. This may be due to the limited number of assays available for oncogene detection, or it may alternately indicate that most of the oncogene families have been identified. The assignment of oncogenes to families was originally based upon their function, structure and sequence homology, or product localization, but the oncogene families appear to be taking on a new significance in the context of their participation in the cell cycle. For instance, the unrestricted proliferation of cells transformed by oncogenes provides a strong argument that their cognate proto-oncogenes and tumor suppressor genes normally function in the regulation of the cell cycle (M. Park et al., *The Metabolic Basis of Inherited Disease*, Vol. 1, E. R. Scriver, A. L. Beaudet, W. S. Sly, and D. Valle, Eds. (McGraw-Hill, New York, 1989), p. 251).

With respect to characterization of members of the oncogene families, recent studies of signal transduction pathways in somatic cells have linked the products of one oncogene family either directly or indirectly to the activation of members of other families. For example, the stimulation of certain growth factor receptors by their appropriate growth factor or ligand results in the association of receptors directly with the src and raf products (Morrison et al., *Cell*, 58, 649–657 (1989); Kypta et al., *Cell*, 62, 481–492 (1990)). The receptors also associate with several proteins involved in second messenger pathways (e.g., PLCγ and PI3 kinase) (Coughlin et al., *Science*, 243, 1191–1194 (1989); Kumjian et al., *Proc. Natl. Acad. Sci. USA*, 86, 8232–8236 (1989); and Margolis et al., *Cell*, 57, 1101–1107 (1989)) as well as with a GTPase activating protein (GAP) that enhances the activity of the ras gene product. (Kaplan et al., *Cell*, 61, 125–133 (1990); Kazlauskas et al., *Science*, 247, 1578–1581 (1990)). Mitogenic stimulation of certain tyrosine kinase growth factor receptors ultimately results in specific transcriptional induction of a well-characterized series of genes, several of which are nuclear oncogenes. (Rollins et al., *Adv. Cancer Res.*, 53, 1–32 (1989); Vogt et al., *Adv. Cancer Res.*, 55, 1–35 (1990); Bravo R., *Cell Growth & Differentiation*, 1, 305–309 (1990)).

In contrast, less progress has been made in understanding how members of the diverse oncogene families elicit expression of the transformed phenotype. The fact that the members of these families function in the same or parallel pathways facilitates assigning hierarchy and determining whether a particular family is "upstream" or "downstream" in the pathway. Growth factors or, for that matter, nuclear transcription regulators are likely not proximal effectors of the transformed phenotype. Assuming that most of the oncogene families have been identified, the most probable candidates for proximal effectors would be members of the kinase oncogene families, since these proteins might modify nuclear and/or cytoskeletal proteins necessary for induction of morphological alterations associated with the neoplastic phenotype. Elucidation of this hierarchy may provide a means to develop strategies to intervene in neoplastic transformation.

Moreover, another major unanswered question concerns how the oncogenes influence the cell cycle. The entry into the S-phase and M-phase is highly regulated and this regulation has been observed in all species from yeast through man. The gene products that mediate and control this regulation are currently being characterized. For instance, the cell cycle has been intensively studied in the budding yeast *Saccharomyces cerevisiae* and the fission yeast *Schizosaccharomyces pombe*. Even though these yeasts are as evolutionarily distant from each other as they are from mammals, certain cell cycle regulators are conserved between these yeasts, not only in structure, but also in function. As an example, the CDC28 and cdc2 genes from the budding and fission yeasts, respectively, are functionally equivalent and encode a serine kinase whose targets are influenced during the cell cycle by the appearance of cyclins. These proteins, which were first discovered in clams and sea urchins were so named because of their cyclic appearance during the cell cycle.

Similarly, an activity termed maturation promoting factor (MPF) was discovered in unfertilized amphibian eggs (Masui et al., *J. Exp. Zool*, 177, 129–146 (1971); Smith et al., *Dev. Biol.*, 25, 233–247 (1971)) as the activity responsible for inducing meiotic maturation, the process by which a fully grown oocyte becomes an egg capable of being fertilized (Masui et al., *Int. Rev. Cytol.*, 57, 185–292 (1979)). MPF was subsequently found from yeast to man in all cells undergoing meiosis or mitosis and is considered the universal regulator of M-phase in eukaryotes (Kishimoto et al., *Exp. Cell Res.*, 137, 121–126 (1982); Kishimoto et al., *J. Exp. Zool.*, 231, 293–295 (1984); Tachibana et al., *J. Cell Sci.*, 88, 273–282 (1987)). MPF is responsible for nuclear envelope breakdown and chromosome condensation (Lohka et al., *J. Cell Biol.*, 98, 1222–1230 (1984); Lohka et al., *J. Cell Biol.*, 101, 518–523 (1985); Miake-Lye et al., *Cell, 41, 165–175* (1985)). Lohka et al. (*Proc. Natl. Acad. Sci. USA*, 85, 3009–3013 (1988)) first purified MPF, which was subsequently shown to consist of cyclins and the homologs of the yeast p34$^{cdc2}$ gene product and related proteins (Gautier et al., *Cell*, 54, 433–439 (1988); Gautier et al., *Cell*, 60, 487–494 (1990)).

Thus, in just a few years, an extraordinary series of discoveries allowed characterization of the major cell cycle regulator, in species as diverse as yeast and man. However, at present, there are more questions than answers in terms of transit of cells through the cell cycle, aberrations of this process such as occur in cancer, and the role of proto-oncogenes, oncogenes and tumor suppressor genes in mediating these processes. The correlation between cell cycle regulation and the normal and aberrant roles of proto-oncogenes, tumor suppressor genes and oncogenes, respectively, in this process suggest oncogenes and mutant tumor suppressor genes are attractive targets for therapeutic intervention. Accordingly, there remains a need for techniques to identify suitable anticancer drugs as well as new and efficacious methods and pharmaceutical compositions for the treatment of cancer in mammals, particularly humans.

Thus, it is an object of the present invention to provide such a method of identifying suitable anticancer drugs and treatments, and in particular, to provide a method of identifying drugs which selectively inhibit the growth of particular cancer cells. It is another object of the present invention to provide methods of using such drugs.

These and other objects and advantages of the present invention, as well as additional inventive features, will be apparent from the description of the invention provided herein.

BRIEF SUMMARY OF THE INVENTION

The present invention provides a method of identifying drugs which selectively inhibit the growth of a particular type of cancer cell containing an activated oncogene, as well as methods of using such drugs, for example, in the selective inhibition of the growth of such a cancer cell, and in the treatment of a patient having such cancer. In particular, the present invention provides a method of identifying a drug which selectively inhibits the growth of a particular type of cancer cell, which method comprises (a) contacting with the drug at least two cancer cells derived from the same type of biological material, wherein the cancer cells differ as to the presence of a particular DNA sequence, (b) measuring the effect of the drug on the growth of the cancer cells, and (c) determining whether there is a correlation between the effect of the drug on the cancer cells and the presence or absence of the DNA sequence in the cancer cells.

Moreover, the invention comprises a new approach for designing combinations of drugs for the treatment of cancer based on the discovery that it is desirable to use a drug which exerts its primary effect on the mammalian cell cycle prior to or during S-phase in combination with a drug that exerts its primary effect after S-phase and prior to or during M-phase. Thus, the present invention also comprises methods in which an S-phase reacting drug specific for a particular type of cancer cell can be employed in conjunction with an M-phase reacting drug also specific for the same type of cancer cell.

The present invention is accordingly based in part on a heretofore unappreciated rationale for why a large number of frequently used antineoplastic drugs are effective in cancer treatment. Namely, oncogene activation or loss of tumor suppressor gene function leads to compromise of "checkpoints" which typically function during cell cycle progression to create pauses in the cell cycle at which the fidelity of the genetic information, or the correct partitioning of this information is checked. The compromise of checkpoint function by oncogenes including tumor suppressor genes results in tumor cells being more vulnerable than normal cells to antineoplastic agents that target substrates both in the M-phase and the S-phase of the cell cycle (Vande Woude et al., In: *Views of Cancer Research*, Fortner et al, eds., (PA: J. B. Lippincott Co., 1990) 128–143; Perkins et al., In: *Cancer: Principles and Practices of Oncology*, 4th ed., DeVita et al., eds., (PA: J. B. Lippincott Co., 1993) 35–57; Murakami et al., In: *The Molecular Basis of Cancer*, Mendelsohn et al., eds., (PA: W. B. Saunders Co., 1994) in press).

DETAILED DESCRIPTION OF THE INVENTION

Figure 1:
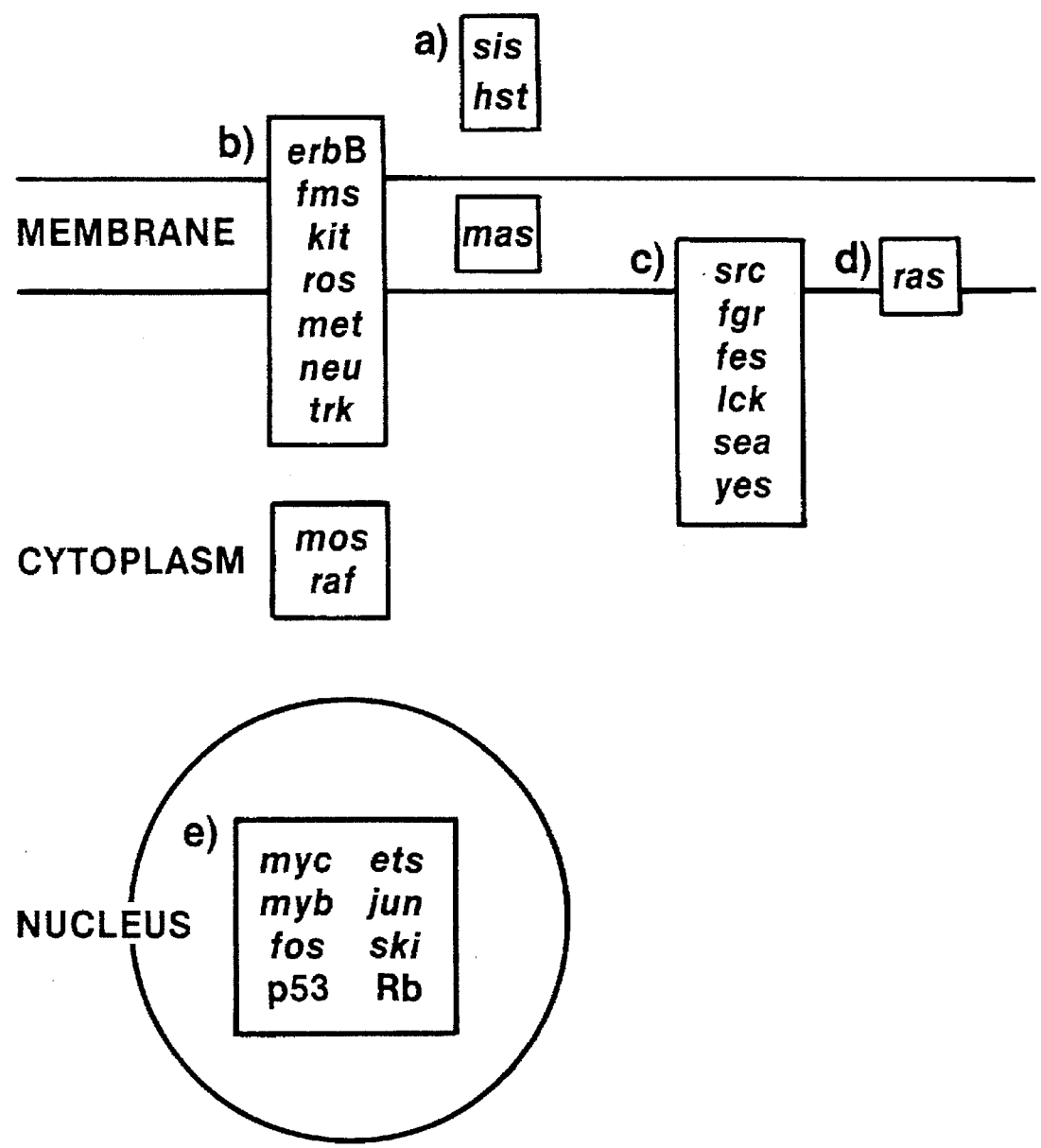
FIG. 1 illustrates the cellular localization of some of the gene products of oncogene, proto-oncogene, and tumor suppressor genes of the oncogene families described in Table 1: (a) growth factors (external mitogenic signals); (b) transmembrane tyrosine kinass growth factor receptors; (c) non-integral membrane-associated proteins of the src gene family; (d) non-integral membrane-associated proteins of the ras gene family; (e) oncogene products localized in the nucleus; and (f) cytoplasmic protein kinase mos and raf.

The present invention concerns a method of identifying drugs which selectively inhibit the growth of particular cancer cells as well as methods of using such drugs.

For ease of reference, the abbreviations used herein are as indicated in Table 2.

TABLE 2

| Abbreviations | |
|---|---|
| cDNA | complementary deoxyribonucleic acid |
| CNS | central nervous system |
| DGGE | denaturing gradient gel electrophoresis |
| DNA | deoxyribonucleic acid |
| MPF | maturation promoting factor |
| NCI | National Cancer Institute |
| PCR | polymerase chain reaction |

Also, the following definitions are employed herein:

Drug—any active agent which has a biological effect on cell growth or cell cycle including, but not limited to, traditional anticancer drugs such as those shown in Table 4, the novel drugs identified in the present invention as capable of selectively inhibiting the growth of particular cancer cells and listed in Table 6, proteins having anticancer activity such as tumor necrosis factor and lymphotoxin, proteins encoded by proto-oncogenes and tumor suppressor genes, antibodies or antibody conjugates which target the activated oncogenes in cancer cells, etc.

S-phase drug—a drug which exerts its primary cytostatic or cytotoxic effect on the mammalian cell cycle prior to or during S-phase.

M-phase drug—a drug which exerts its primary cytostatic or cytotoxic effect on the mammalian cell cycle after S-phase and prior to or during M-phase.

Tumor suppressor gene—a gene which negatively regulates normal cell function.

Proto-oncogene—a gene which positively regulates normal cell function.

Oncogene—altered form or expression of a proto-oncogene or tumor suppressor gene which leads to a transformed phenotype in a cell and/or tumor formation. Transformation is promoted through the gain of function of proto-oncogenes and loss of function of tumor suppressor genes.

Transformed phenotype—a phenotype which is not characteristic of a normal (non-cancerous) cell which includes loss of contact inhibition, altered morphology and loss of genetic stability.

Metaphase—the stage of mitosis or meiosis when chromosomes are aligned along the equatorial plane of the spindle.

Interphase—the state of the eukaryotic nucleus when it is not engaged in mitosis or meiosis; consists of $G_1$, S, and $G_2$ periods in cycling cells.

Proto-oncogenes and tumor suppressor genes appear to be involved in controlling the growth of cells. Accordingly, an understanding of the normal role of proto-oncogenes and tumor suppressor genes provides insight on the mechanism by which activated oncogenes and inactivation of tumor suppressor genes can affect cell growth, tumor formation and the phenotypes of transformed cells.

In the context of the present invention, for example, the inappropriate expression of the mos oncogene during interphase in somatic cells may lead to the expression of M-phase phenotypes at all stages of the somatic cell cycle. This proposed activity of the mos oncogene is consistent with the normal activities of the mos proto-oncogene during oocyte meiotic maturation (Yew et al., Current Opinions in Genetics and Development, 3, 19–25 (1993)). Namely, the product of the mos proto-oncogene is a serine/threonine kinase that is expressed at high levels in germ cells. Mos is a regulator of meiotic maturation, and is required for the initiation and progression of oocyte meiotic maturation that leads to the production of unfertilized eggs. Mos is also a component of cytostatic factor, an activity that appears to arrest oocyte maturation at meiotic metaphase II. There is evidence that the Mos protein is associated with tubulin in unfertilized eggs and transformed cells, which may indicate that Mos is involved in the microtubular reorganization that occurs during M-phase.

The inappropriate expression of Mos M-phase activity during interphase of the cell cycle may be responsible for the transforming activity of Mos. For example, in mos-transformed cells, the altered cell morphology may equate with the cytoskeletal changes that occur normally during mitotic rounding. Genetic instability of transformed cells as presented in Table 3 could be due to premature chromatin condensation events.

TABLE 3

Properties of the Transformed Phenotype

Cellular Morphology

Nuclear structure
Cytoskeleton

TABLE 3-continued

Properties of the Transformed Phenotype

Growth Characteristics and Cell Metabolism

Anchorage independence and loss of contact inhibition
Changes in extracellular matrix
Growth factor independence
Genetic Instability Consistent with these ideas is the suggestion that genetic instability reflects a failure in the cell cycle checkpoint function, as has been described in yeast (Hartwell et al., Science, 246, 629–634 (1989)). These checkpoints are pauses that occur at specific points in the cell cycle for purposes of correcting errors, such as in the fidelity of replicated DNA. While mutations in the checkpoint genes could result in a high frequency of mutations that lead to malignant transformation (Hartwell et al., Science, 246, 629–634 (1989)), the activation of an oncogene could compromise checkpoint function anywhere in the cell cycle. For example, the constitutive expression of the mos oncogene throughout the entire cell cycle could override the normal cell cycle program and abrogate normal checkpoint function. This disruption of normal cell cycle function provides an explanation both for the genetic instability of tumor cells and for the greater sensitivity of tumor cells to chemotherapeutic agents compared to non-tumor cells.

A number of oncogenes induce morphological transformation similar to that induced by mos and may function in the same or parallel pathways. For example, the inventors have investigated whether the ras oncogene product also has M-phase activities. This observation would indicate that constitutive M-phase activity proposed as an explanation for the mos-transformed phenotype may be more general. Several years ago, it was shown that the activated ras oncogene could induce meiotic maturation in Xenopus (Birchmeier et al., Cell, 43, 615–621 (1985)). The inventors have extended these experiments and have demonstrated that the ras oncogene, like mos, also displays M-phase activity (I. Daar et al., Science, 253, 74–76 (1991)). Thus, the Harvey ras oncogene product injected into cleaving blastomeres arrests cleavage at metaphase. This arrest occurs in the absence of mos product, demonstrating that parallel pathways to metaphase arrest exist (Barrett et al., Mol. Cell. Biol. 10, 310–315 (1990); I. Daar et al., Science, 253, 74–76 (1991)). It is not clear how the ras oncoprotein induces stabilization of MPF, but it does so efficiently, consistent with its ability to induce meiotic maturation.

While oncogenes have provided a common thread woven through all of the cancer research disciplines, there has been a lack of correlation between oncogenes and tumor suppressor genes and the effect of antineoplastic drugs. If oncogenes including tumor suppressor genes are the genes responsible for neoplastic transformation, then the ability of antineoplastic drugs to specifically target cancer cells versus normal cells, and particularly cancer cells containing specific activated oncogenes, would suggest that these drugs target the alterations imposed by oncogenes, as well as the specific oncogenes themselves.

There has been a sustained interest in how antineoplastic drugs connect with the cell cycle (Hellman et al., in: DeVita, Jr. et al., (eds.), *Cancer: Principles and Practices of Oncology*, 1st Ed., (PA: J. B. Lippincott, (1982) 73–79). Accordingly, the inventors have investigated how these drugs relate to the influences of oncogenes on the cancer cell. For example, the M-phase acting drug taxol stabilizes tubulin polymers or contributes to the polymerization of tubulin. If mos and other oncogenes that are effectors of the transformed phenotype do so, in part, through modification of tubulin (as has been suggested for mos), the superimposition of M-phase function on all stages of the cell cycle of transformed cells suggests how taxol might selectively work against certain cancer cells as compared with normal cells.

Based on the research of the inventors, it is now possible to ask whether there is a relationship between antineoplastic drug targets and oncogene product-mediated alterations of the cell cycle. The inventors have placed a number of antineoplastic drugs as either upstream or downstream reacting compounds as illustrated in Table 4 based on a survey of the relevant literature. The inventors recognize that the drugs may function at different stages and on multiple targets in the cell cycle.

TABLE 4

Selected Anti-neoplastic Agents

| $G_1$ + S-phase (Upstream) | M-phase (Downstream) |
| --- | --- |
| Tamoxifen (anti-estrogen) | Vincristine (tubulin binding) |
| Prednisone (corticosteroid) | Vinblastine (tubulin binding) |
| Decarbazine (DNA alkylation) | Taxol (tubulin binding) |
| Mechlorethamine (DNA alkylation) | Doxorubicin (topoisomerase II inhibitor) |
| Cis platinum (DNA cross-linking) | Daunorubicin (topoisomerase II inhibitor) |
| Methotrexate (DNA synthesis) | Etoposide (topoisomerase II inhibitor) |
| 5'-Fluorouracil (DNA synthesis) | Bleomycin (DNA cross-linking) |
| Cytosine arabinoside (DNA synthesis) | |

The consideration of whether the oncogenes function upstream or downstream in the cell cycle may have important implications in drug therapy. Specifically, the possibility for tumor cells to develop drug resistance and escape the cytotoxic or cytostatic effect of a given drug should be less if the drug target is downstream in the cell cycle. The inventors have suggested that drugs like DNA alkylating agents may preferentially target tumor cells over normal cells if the cell cycle checkpoint function (Hartwell et al., *Science*, 246, 629–634 (1989)) in tumor cells has been compromised. For example, if repair of DNA alkylation damage would be compromised the cell would proceed through the cycle carrying the mutagenic damage in its genome. Ultimately, propagation of this damage could result in a cytotoxic or cytostatic effect. In addition, the sensitivity of tumor cells to antineoplastic drugs that target M-phase activity, like tubulin-specific agents and topoisomerase II inhibitors, might be mediated by the gain in function due to oncogene-induced M-phase activity.

Certain antineoplastic agents are recognized to act synergistically (DeVita, Jr., Principles of Chemotherapy. In: *Cancer: Principles and Practice of Oncology*, 1st edition, DeVita, Jr. VT, Hellman S, Rosenberg SA (eds.), (PA: J. B. Lippincott, 1982) 132–155). The metabolic basis of synergy, for example, between 5- fluorouracil and methotrexate is understood (Cadman et al., *Science*, 50, 711–716 (1984)). The cause of synergy between other drugs, however, is not so clear. Certain drugs can be assigned as having chiefly S-phase or M-phase activity, and a possible explanation emerges regarding their synergistic action. Agents acting on targets that are sequential in the cell cycle would be expected to act in synergy: an agent that acts in S-phase might be expected to synergize with M-phase agents resulting in irreversible cytotoxic or cytostatic damage to the treated cell. Using this rationale, many chemotherapeutic protocols can be shown to be combinations of S-phase and M-phase agents, as illustrated in Table 5.

TABLE 5

Selected Chemotherapautic Regimens

| Malignancy | $G_1$ or S-phase (Upstream) | M-phase (Downstream) |
| --- | --- | --- |
| Acute Lymphocytic Leukemia | Prednisone | Vincristine |
| | L-Asparaginase | Daunorubicin |
| | Cytosine Arabinoside | Etopsoside |
| Acute Nonlymphocytic Leukemia | Cytosine Arabinoside | Daunorubicin |
| Testicular Cancer | Cis Platinum | Bleomycin |
| | | Vinblastine or Etoposide |
| Hodgkins Lymphoma | Mechlorethamine | |
| | Procarbazine | Vincristine |
| | Prednisone | |
| | | Doxorubicin |
| | Dacarbazine | Vincristine |
| | | Bleomycin |

For example, acute non-lymphocytic leukemia, testicular cancer, and Hodgkins lymphoma are tumors that are treated with drugs from both categories. Further, the preponderance of either S-phase or M-phase agents in MOPP and ABVD regimens for Hodgkins lymphoma might explain the efficacy of one drug regimen as salvage chemotherapy after the other has failed.

The inventors have proposed that the growth of oncogene-transformed cells may be completely inhibited by the combination of a drug having S-phase activity and a therapeutic effect of a drug having M-phase activity (Vande Woude et al., In: *Views of Cancer Research*, Fortner et al., eds., (PA: J. B. Lippincott Co., 1990) 128–143). Knowing how oncogenes function in the cell cycle can be used not only to elucidate mechanisms for currently used drugs, but also may aid in the design of drugs in the future. Based on this premise, the inventors have tried to explain interactions between cell cycle, oncogenes and antineoplastic drugs. The studies of the inventors suggest a direct link between oncogenic transformation, cell cycle activity, and antineoplastic drugs. The sensitivity of certain cancers to the empirically established chemotherapeutic protocols may be related to the oncogene activated and its influence on the cell cycle.

Accordingly, the present invention provides a method of identifying a drug which selectively inhibits the growth of a particular type of cancer cell comprising a particular DNA sequence. This method comprises: (a) contacting with the drug at least two cancer cells derived from the same type of biological material, wherein the cancer cells differ as to the presence or absence of a particular DNA sequence; (b) measuring the effect of the drug on the growth of the cancer cells; and (c) determining whether there is a correlation between the effect of the drug on the cancer cells and the presence or absence of the DNA sequence in the cancer cells.

In the context of the present invention, a drug inhibits the growth of a particular type of cancer cell when it exerts a cytotoxic and/or cytostatic effect on the growth of that particular type of cancer cell (e.g., lung or CNS cancer). Cancer cells are considered of the same type of biological material if they are derived (i.e., meaning generated as the result of some type of permanent change in a normal cell) from the same type of biological material. "Biological material", as used in the context of the present invention, means any normal cell type (e.g., lung cell, colon cell, brain cell, blood cell, etc.) at any stage of maturation or development (e.g., a stem cell as compared with a fully differentiated cell). Thus, contacting a drug with at least two cancer cells derived from the same type of biological material, wherein the cancer cells differ as to the presence or absence of a particular DNA sequence, refers to, for example, at least two colon cancer cells or at least two lung cancer cells which differ as to the existence of a particular DNA sequence. In other words, the drug contacts at least two cancer cells which are the same tumor-type specific cancer cells but which differ as to the presence or absence of a particular DNA sequence, i.e., which are not the same DNA sequence-type specific cancer cells.

The DNA sequence of interest in the context of the present invention can be any DNA sequence whose existence in a cancer cell can be potentially correlated with the effectiveness of a drug against the cancer cell. In general, the DNA sequence will comprise an activated oncogene (i.e., an oncogene comprising a gain of function mutation) or an oncogenic tumor suppressor gene (i.e., a tumor suppressor gene comprising a loss of function mutation). While the DNA sequence can comprise any oncogene including a tumor suppressor gene, the DNA sequence preferably comprises the ras oncogene (and in particular K-ras-2), which, more preferably, has been activated by a mutation in the 12th, 13th or 61st codon.

The GenBank® Data Bank Accession Numbers for various ras sequences are as follows: K-ras exon 1 sequence, Accession Number L00045 (Locus: HUMRASK02); K-ras exon 2 sequence, Accession Number L00046 (Locus: HUMRASK03); N-ras exon 1 sequence, Accession Number X00642 (Locus: HSNRAS1); N-ras exon 2 sequence, Accession Number X00643 (Locus: HSNRAS2); H-ras full length sequence, Accession Number V00574 (Locus: HSRAS1).

Analysis of oncogene sequences to detect any departure from the wild-type status can be done using the methods outlined herein (i.e., DGGE and direct DNA sequencing) as well as improvements on those methods and such other methods as are known to those of ordinary skill in the art. Primers which can be employed for sequence analysis of the ras gene are set forth in the Sequence Listing as follows: GC-clamp, SEQ ID NO:1; 5' primer for exon 1 of K-ras-2, SEQ ID NO:2; 3' primer for exon 1 of K-ras-2, SEQ ID NO:3; 3' primer (containing the GC-clamp) for exon 1 of K-ras-2, SEQ ID NO:4; 5' primer for exon 2 of K-ras-2, SEQ ID NO:5; 5' primer (containing the GC-clamp) for exon 2 of K-ras-2, SEQ ID NO:6; 3' primer for exon 2 of K-ras-2, SEQ ID NO:7; 5' primer for exon 1 of N-ras, SEQ ID NO:8; 3' primer for exon 1 of N-ras, SEQ ID NO:9; 3' primer (containing the GC-clamp) for exon 1 of N-ras, SEQ ID NO:10; 5' primer for exon 2 of N-ras, SEQ ID NO:11; 5' primer (containing the GC-clamp) for exon 2 of N-ras, SEQ ID NO:12; 3' primer for exon 2 of N-ras, SEQ ID NO:13; 5' primer for exon 1 of H-ras-1, SEQ ID NO:14; 3' primer for exon 1 of H-ras-1, SEQ ID NO:15; 3' primer (containing the GC-clamp) for exon 1 of H-ras-1, SEQ ID NO:16; 5' primer for exon 2 of H-ras-1, SEQ ID NO:17; 3' primer for exon 2 of H-ras-1, SEQ ID NO:18; 3' primer (containing the GC-clamp) for exon 2 of H-ras-1, SEQ ID NO:19. Also, these primer sequences, except for the GC clamp sequence (SEQ ID NO:1), are set forth in Abrams et al., *Genes, Chromosomes & Cancer*, 6, 73–85 (1993) and Suzuki et al., Oncogene, 5, 1037–1043 (1990).

In accordance with the method of the present invention of identifying drugs which selectively inhibit the growth of a particular type of cancer cell comprising a particular DNA sequence, the cells preferably are contacted in vitro. Contacting will be done under any suitable conditions such as are appropriate for a particular cell lines. For example, drug concentration may need to be reduced in suspensious cell cultures (e.g., leukemia cell cultures) which are in contact with a drug in media on all surfaces, as compared with adherent cell cultures, which are in contact with a drug only on surfaces which are not adhered to a tissue culture substrate. Contacting with a drug is to be done using at least two cancer cells derived from the same type of biological material but will preferably be carried out using a multiplicity of such cancer cells derived from the same type of biological material (e.g., a series of lung cancer cells or a series of colon cancer cells), which cancer cells differ as to the presence or absence of a particular DNA sequence as described above.

In the method of the present invention, the existence of a correlation can be revealed by any suitable means, such as by the calculation of the Pearson and/or Spearman correlation coefficient for the sensitivity of each cell line to a particular drug. This can be preferably done using the COMPARE computer program designed for analyses involving cell lines of the NCI panel.

Representative cell lines which may be employed in the present invention include cell lines comprising the NCI panel of cancer cells, which are given in Table 8. Preferred cancer cells according to the methods of the present invention include non-small cell lung cancer cells and colon cancer cells. However, any suitable cell line can be employed in the context of the present invention. Moreover, cell lines can be generated by transfecting cancer cell lines with activated oncogenes.

The inventors have discovered that cells transformed with certain oncogenes are more sensitive to chemotherapeutic agents than the parental cell line. The correlation between the different oncogenes and the sensitivities which they confer upon particular cancer cells derived from the same type of biological material to different chemotherapeutic agents is of use in designing new chemotherapeutic combinations and agents and in predicting which human tumor cell lines with known activated oncogenes are sensitive to which agents or combinations of agents.

In the context of the present invention, many means can be employed to introduce an activated oncogene into a cancer cell line in vitro. Such methods are well known to those of ordinary skill in the art. Namely, the oncogene can be introduced in the form of nucleic acid, (i.e., genomic deoxyribonucleic acid (DNA) or complementary ribonucleic acid (cDNA)). The nucleic acid can be derived from any source, can be single- or double-stranded, and can optionally contain synthetic, non-natural, or altered nucleotides which are capable of being incorporated into the structure of the DNA or cDNA. The nucleic acid of the present invention is preferably a segment of DNA containing sequences coding for an activated oncogene.

The nucleic acid can be introduced by means of alternative vectors. For example, inserts can be in vectors of different nature, such as phages, viral capsids, plasmids, cosmids, phagemids, YACs, or even attached to the outside of a phage or viral capsid. The vectors can differ in host range, stability, replication, and maintenance. Moreover, the vectors can differ in the types of control exerted over cloned inserts. For example, vectors can place cloned inserts under the control of a different promoter, enhancer, or ribosome binding site, or even organize it as part of a transposon or mobile genetic element.

The vectors can be introduced into the host cell by any suitable means. For instance, with eukaryotic cells, vectors may be introduced through the use of electroporation, transfection, infection, DNA coated microprojectiles, protoplast fusion, microinjection, liposome-mediated transformation, etc.

The form of the introduced nucleic acid may vary with the method used to introduce the vector into a host cell. For example, the nucleic acid may be closed circular, nicked, or linearized, depending upon whether the vector is to be maintained as an autonomously replicating element, integrated as provirus or prophage, transiently transfected, transiently infected as with a replication-disabled virus or phage, or stably introduced through single- or double-crossover recombination events. These methods of introducing an activated oncogene into a host cell in vitro are well known to those of ordinary skill in the art.

The present invention also provides novel drugs identified by the method of the present invention as capable of specifically inhibiting the growth of a particular type of cancer cell which comprises an activated ras oncogene. The chemical structures of the drugs are set forth in Table 6.

TABLE 6

Novel drugs exhibiting a cancer cell-specific effect

| NSC Number | Chemical Name |
|---|---|
| 7364 | Methodichlorophen |

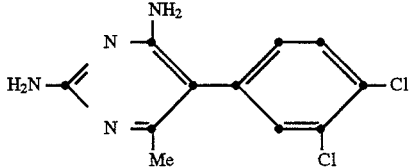

| 63878 | Cytosine Arabinoside |

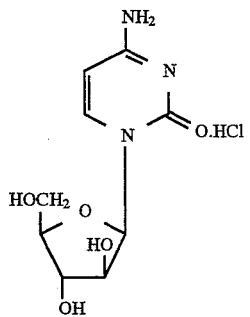

| 134679 | Bizelesin |

TABLE 6-continued
Novel drugs exhibiting a cancer cell-specific effect
| NSC Number | Chemical Name |
|---|---|
| | 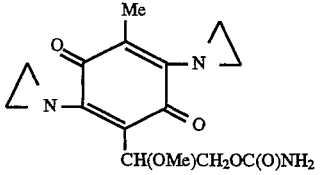 |
| 141540 | Epipodophyllotoxin VP-16213 (VP-16) |
| | 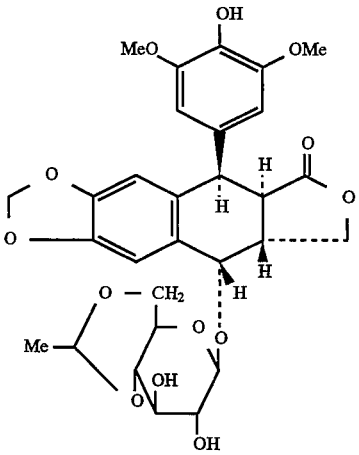 |
| 145668 | Cyclocytidine |
| | 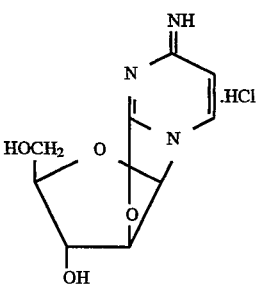 |
| 284682 | 3'-Hydroxydaunorubicin |
| | 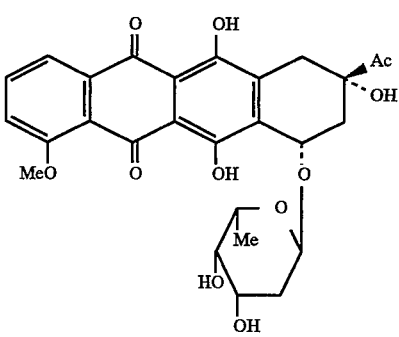 |
| 303812 | Aphidicolin Glycinate |

TABLE 6-continued
Novel drugs exhibiting a cancer cell-specific effect
| NSC Number | Chemical Name |
|---|---|
| | 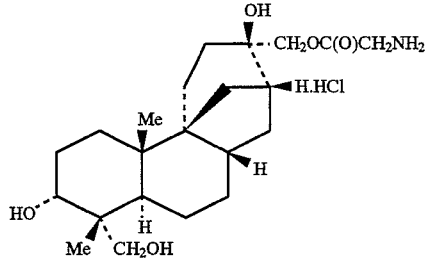 |
| 317003 | 9H-Thioxanthen-9-one, 1-[[2-(dimethylamino)ethyl]amino]-7-hydroxy-4-methyl-, monohydriodide |
| | 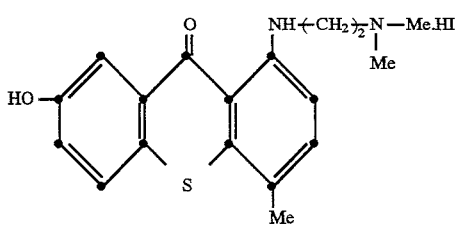 |
| 352122 | Trimetrexate |
| | 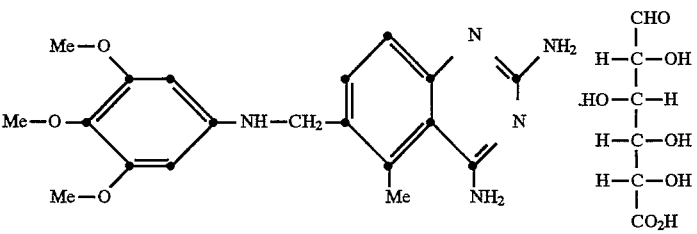 |
| 375575 | Cyclopentenylcytosine |
| | 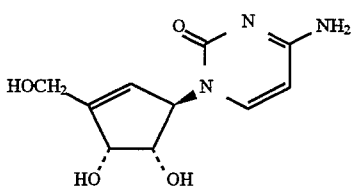 |
| 603335 | 2-Pyridone, 3-Chloro-4-hydroxy-1-β-d-ribofuranosyl |
| | 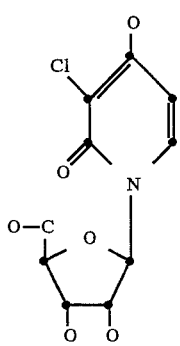 |
| 615291 | 2 CC-1065 Analog |

TABLE 6-continued
Novel drugs exhibiting a cancer cell-specific effect
| NSC Number | Chemical Name |
|---|---|
| 619029 | 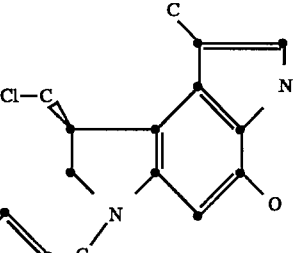 |
| 631522 | 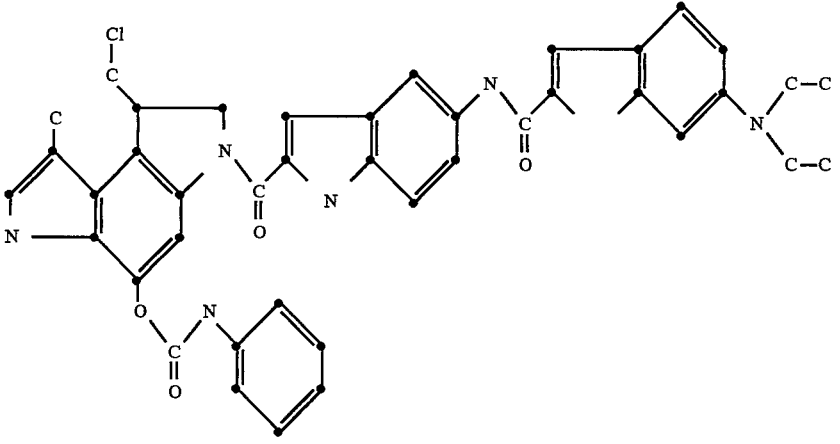 |
| 632246 | 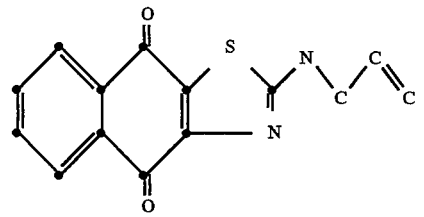 |
| 638855 | 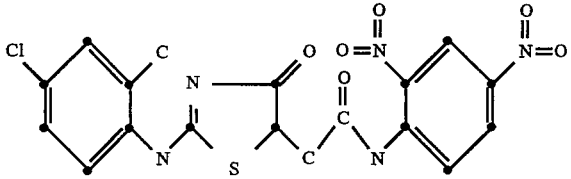 Carbazilquinone |

TABLE 6-continued
Novel drugs exhibiting a cancer cell-specific effect
| NSC Number | Chemical Name |
|---|---|
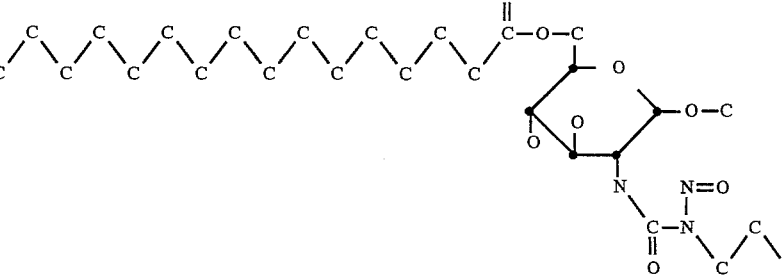
641548                                                    Betuletol
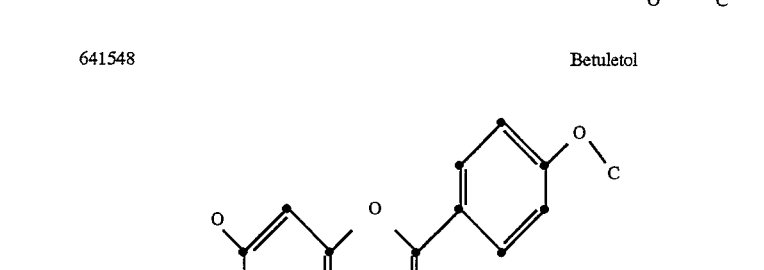
642049
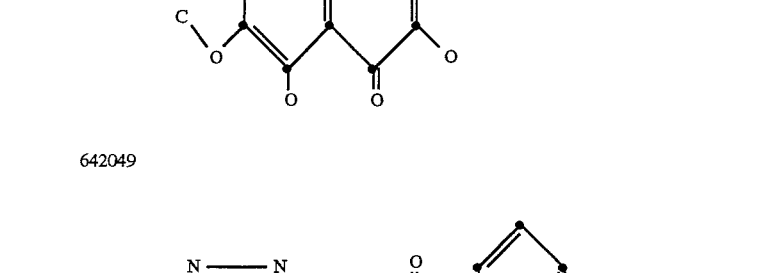
642321
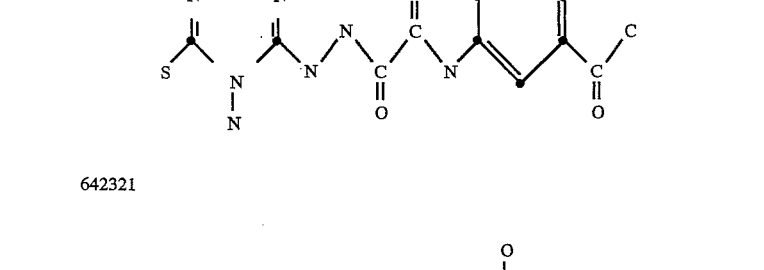
648338

TABLE 6-continued
Novel drugs exhibiting a cancer cell-specific effect
| NSC Number | Chemical Name |
|---|---|
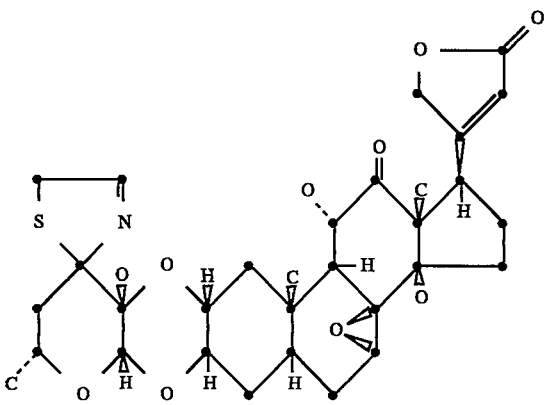
650362
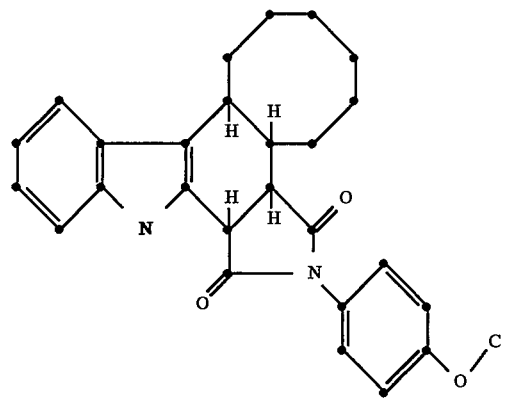
650931
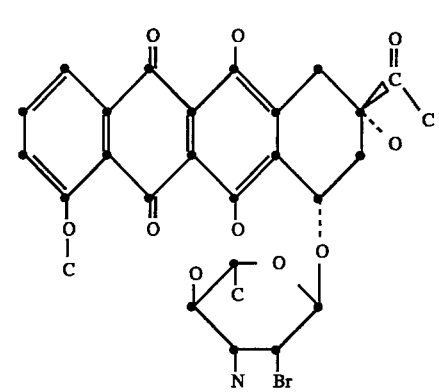
652173
2'-Bromo-4'-epi-daunorubicin TABLE 6-continued Novel drugs exhibiting a cancer cell-specific effect

| NSC Number | Chemical Name |
|---|---|

652565

654236

656239

656240

TABLE 6-continued
Novel drugs exhibiting a cancer cell-specific effect
| NSC Number | Chemical Name |
|---|---|
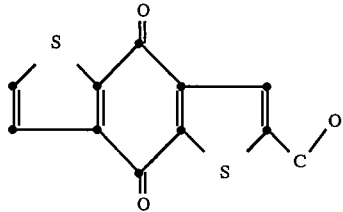
659687
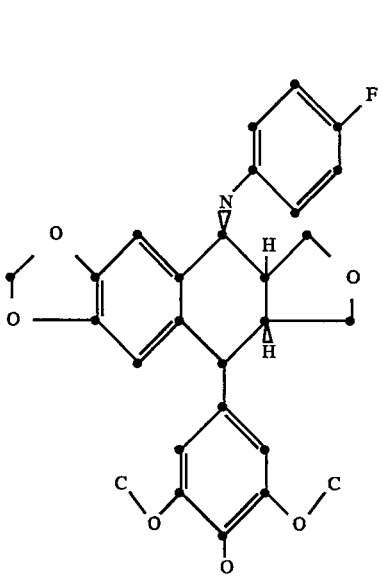
660027
660028

TABLE 6-continued

Novel drugs exhibiting a cancer cell-specific effect

| NSC Number | Chemical Name |
|---|---|
| 663337 | 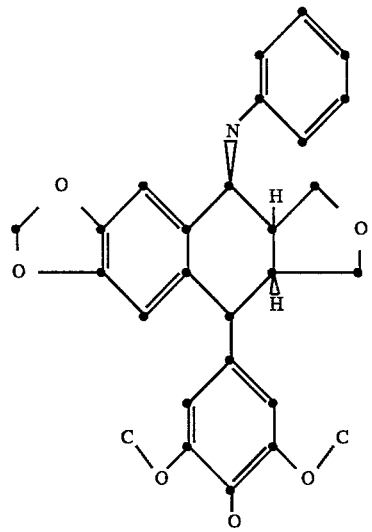 |
| 667730 | 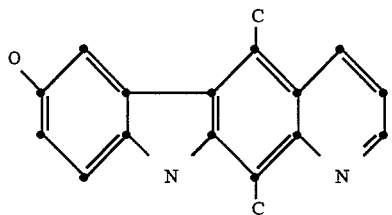 |
| | 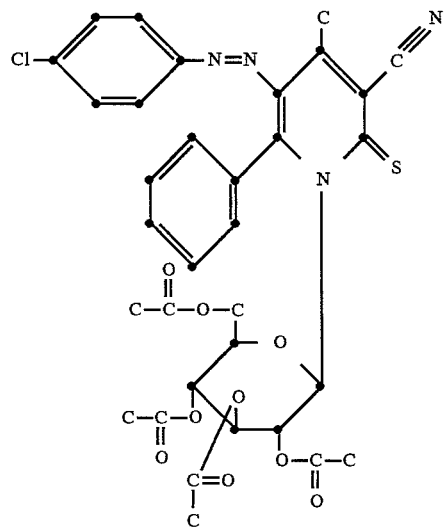 |

Thus, the present invention also provides a method of selectively inhibiting the growth of a non-small cell lung cancer cell or a colon cancer cell comprising an activated ras oncogene, which method comprises contacting said cancer cell with a drug selected from the group consisting of NSC Number 7364, NSC Number 63878, NSC Number 134679, NSC Number 141540, NSC Number 145668, NSC Number 284682, NSC Number 303812, NSC Number 317003, NSC Number 352122, NSC Number 375575, NSC Number 603335, NSC Number 615291, NSC Number 619029, NSC Number 631522, NSC Number 632246, NSC Number 638855, NSC Number 641548, NSC Number 642049, NSC Number 642321, NSC Number 648338, NSC Number 650362, NSC Number 650931, NSC Number 652173, NSC Number 652565, NSC Number 654236, NSC Number 656239, NSC Number 656240, NSC Number 659687, NSC Number 660027, NSC Number 660028, NSC Number 663337 or NSC Number 667730.

In addition, the present invention provides a method of treating cancer in a patient. In a preferred method of the present invention, such method of treatment comprises: (a) isolating from the patient a cancer cell of a particular biological material; (b) detecting the presence of a particular DNA sequence in the cancer cell which is not possessed by other cancer cells derived from the same biological material; and (c) administering a therapeutically effective amount of a drug to the patient which selectively inhibits the growth of the cancer cell as compared to other cancer cells derived from the same biological material. In other words, the drug selectively inhibits the growth of the cancer cell isolated from the patient as compared to the same tumor-type specific cancer cells which differ as to the absence of the particular DNA sequence in the cancer cell isolated from the patient, i.e., as compared to the same tumor-type specific cells which are not the same DNA sequence-type specific cancer cells.

In other preferred methods of treating cancer according to the present invention, the DNA sequence comprises an activated ras oncogene, and the cancer cell is selected from the group consisting of non-small cell lung cancer cells and colon cancer cells.

The drug administered to the patient in the context of the present invention will selectively inhibit the growth of the cancer cell containing a particular DNA sequence (e.g., an activated oncogene or oncogenic tumor suppressor gene) as compared to other cancer cells derived from the same biological material which do not contain the particular DNA sequence. Generally, the two different types of cancer cells derived from the same biological material (e.g., two different types of lung or colon cancer cells) will not be present in the same patient. Such a drug which is capable of selectively inhibiting the growth of a particular cancer cell which is derived from a certain biological material and contains a particular DNA sequence (e.g., a lung cancer cell with an activated ras oncogene) will also preferably be selective not only with respect to other cancer cells derived from the same biological material which do not possess the particular DNA sequence (e.g., lung cancer cells which do not include an activated ras oncogene) but also as compared to other cancer cells not derived from the same biological material which do or do not contain the particular DNA sequence (e.g., colon cancer cells).

The drugs employed in the method of treatment of the present invention may be used in the form of their pharmaceutically acceptable salts, may be used alone or in appropriate association, and also may be used in combination with other pharmaceutically active compounds.

The drug may be present in the pharmaceutical composition in any suitable quantity. The pharmaceutically acceptable excipients described herein, for example, vehicles, adjuvants, carriers or diluents, are readily available to the public.

One skilled in the art will appreciate that suitable methods of administering a drug of the present invention to a patient or laboratory animal are available, and, although more than one route can be used to administer a particular drug, a particular route can provide a more immediate and more effective reaction than another route. Pharmaceutically acceptable excipients are also well-known to those who are skilled in the art, and are readily available. The choice of excipient will be determined in part by the particular drug, as well as by the particular method used to administer the composition. Accordingly, there is a wide variety of suitable formulations of the pharmaceutical compositions of the present invention. The following methods and excipients are merely exemplary and are in no way limiting. However, pharmaceutically acceptable excipients which do not negate the therapeutic effects of the drugs employed for therapy are preferred.

Formulations suitable for oral administration can consist of (a) liquid solutions, such as an effective amount of the drug dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The drugs of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Preferred methods of administration of drugs are by intravenous injection, bolus injection, continuous infusion, or delivery from an osmotic pump.

The dose administered to a patient or laboratory animal, and particularly a human, in the context of the present invention should be sufficient to effect a prophylactic or therapeutic response in the animal over a reasonable time frame. One skilled in the art will recognize that dosage will depend on a variety of factors including the strength of the particular drug employed, the condition of the patient or animal being treated, the body weight of the patient or animal, as well as the severity and stage of the cancer. The size of the dose will also be determined by the existence, nature, and extent of any adverse side-effects that might accompany the administration of a particular drug. Suitable doses and dosage regimens can be determined by comparisons to well known anticancer agents (such as described in standard pharmacology text like *Goodman and Gilman's:*

*The Pharmacological Basis of Therapeutics*, 7th ed., Gilman et al., eds., (New York: MacMillan Publishing Co., 1985), as well as standard texts employed by physicians in the treatment of cancer) known to effect the desired anticancer response.

Specifically, a suitable dose (i.e., a dose which is "therapeutically effective") is that which will result in a concentration of the active agent (in blood and/or tissues) which is known to reduce growth of the cancer cell as measured by any standard means. The preferred dosage is the amount which results in a reduction in cancer cell growth without significant side effects. This preferred dosage may differ per patient and depending on the drug concentrations employed.

This method of treatment of the present invention can be coupled with the method of drug identification of the present invention. For instance, the drug which selectively inhibits the growth of the particular type of cancer cell comprising the particular DNA sequence can be identified by: (a) contacting with the drug at least two cancer cells derived from the same type of biological material, wherein the cancer cells differ as to the presence of a particular DNA sequence; (b) measuring the effect of the drug on the growth of the cancer cells; and (c) determining whether there is a correlation between the effect of the drug on the cancer cells and the presence or absence of the DNA sequence in the cancer cells.

Further, in another preferred method of the present invention, the drug employed for treatment of a patient (in particular, a patient having a non-small cell lung cancer or colon cancer wherein the cancer cells contain an activated ras oncogene) is selected from the group consisting of NSC Number 7364, NSC Number 63878, NSC Number 134679, NSC Number 141540, NSC Number 145668, NSC Number 284682, NSC Number 303812, NSC Number 317003, NSC Number 352122, NSC Number 375575, NSC Number 603335, NSC Number 615291, NSC Number 619029, NSC Number 631522, NSC Number 632246, NSC Number 638855, NSC Number 641548, NSC Number 642049, NSC Number 642321, NSC Number 648338, NSC Number 650362, NSC Number 650931, NSC Number 652173, NSC Number 652565, NSC Number 654236, NSC Number 656239, NSC Number 656240, NSC Number 659687, NSC Number 660027, NSC Number 660028, NSC Number 663337 or NSC Number 667730.

In yet another preferred method of treatment according to the present invention the drug comprises a combination of a drug which exerts its primary effect prior to or during S-phase and a drug which exerts its primary effect after S-phase and prior to or during M-phase.

This method of treatment is based on the principle that certain anticancer drugs, and in particular combinations of anticancer drugs, are effective because they take advantage of a cancer cell's inability to repair itself and/or a cancer cell's inability to check the cell cycle to ensure the proper order of cell cycle events. The known check points in the cell cycle are summarized in Hartwell et al., *Science*, 246, 629–634 (1989). It may be desirable to use drugs which act at different checkpoints in combination therapy to treat cancer in an effort to achieve a complimentary anticancer effect which could not be achieved if the drugs were used alone or if two drugs which affect the same checkpoint are used together.

The drugs identified by the method of the present invention as selectively inhibiting particular cancer cells can be screened for their ability to interfere with the mammalian cell cycle prior to or during S-phase and for their ability to interfere with the mammalian cell cycle after S-phase and prior to or during M-phase. Several of the drugs have already been identified as S-phase or M-phase reacting drugs, as illustrated in Table 13, and their possible mechanism of action has been elucidated, as depicted in Table 12. The drugs appear to fall into four main classes based on possible mechanisms of action: (1) pyrimidine analogs and pyrimidine biosynthesis inhibitors; (2) antifolates; (3) topoisomerase II inhibitors; and (4) alkylating agents. This suggests the drugs may be useful in treatment, particularly when employed in synergistic combinations. According to the present invention, an S-phase drug can then be used together with an M-phase drug for further screening to see if a synergistic anti-cancer effect is observed. If such an anti-cancer effect is observed, additional screening and testing on this combination can be conducted to determine whether or not the combination of drugs is therapeutically useful in a patient.

For combinations which are determined to be effective, the two drugs (i.e., the "S-phase" drug and the "M-phase" drug) can be administered to a patient (or a laboratory mammal such as a mouse, rabbit, hamster, guinea pig, etc.) at the same time as part of the same pharmaceutical composition, or the two drugs can be administered to the patient in close proximity in time to each other so that a suitable level of both drugs is present in the patient whereby a synergistic effect can be achieved. Usually, the two drugs will be administered to the patient within 24 hours of each other, preferably within 8 hours of each other and more preferably within 1 hour of each other. The exact timing of administration may be affected by the half-life of the drugs, the toxicity of the drugs, etc. Known drugs will preferably be administered by the routes of administration and dosages currently approved by the FDA. However, when a synergistic effect is observed between two drugs, it is possible that each drug can be administered in a dosage which is lower than the dosage used when the drug is administered alone.

The following examples further illustrate the present invention but, of course, should not be construed as in any way limiting its scope.

EXAMPLE 1

Determining the status of ras genes contained within transformed cell lines

In this Example, the status of an oncogene contained within representative transformed human cells was investigated. The ras gene was studied as a representative oncogene.

The 60 human tumor cell lines employed in this study, as well as conditions for their maintenance and culture in vitro have been described previously (Monks et al., *J. Natl. Cancer Inst.*, 83, 757–766). The cell lines (hereinafter collectively termed "the NCI panel") comprise the panel of human tumor cell lines currently used in the investigational, disease-oriented, in vitro drug-discovery screen being implemented by the National Cancer Institute (NCI). The purpose of this screen is to initially evaluate for cytotoxic and/or cytostatic activity against different types of tumors more than 10,000 new substances per year (Monks et al., *J. Natl. Cancer Inst.*, 83, 757–766; Boyd, *Cancer: Princ. Pract. Oncol. Update*, 3(10), 1–12 (1989)). Data on the activity of the new drugs is collected within the NCI database, with each new drug being assigned an "NSC Number".

The ras genes contained within cell lines of the current NCI panel were analyzed. As presented in Table 1, the ras gene family is comprised of three genes, H-ras, N-ras and K-ras. Within humans, H-ras-1 and K-ras-2 have been mapped to the short arms of chromosomes 11 and 12, respectively, and N-ras has been mapped to the short arm of chromosome 1 (Barbacid, *Ann. Rev. Biochem.*, 56, 779–827 employed for PCR were specific for each intron/exon junction as set forth in Table 7.

TABLE 7

PCR Primers for the DGGE and Direct DNA Sequencing Anaylsis of rasGenes

| rasGene | | Exon Sequence (5'→3') |
|---|---|---|
| K-<u>ras</u>-2 | 1 | 5' Primer: (for DGGE and DNA sequencing) GGCCTGCTGAAAATFACTGA<br>3' Primer: (for DNA sequencing) GTCCTGCACCAGTAATATCG<br>3' Primer: (for DGGE) GC clamp-GTCCTGCACCAGTAATATGC |
| | 2 | 5' Primer: (for DNA sequencing) CCAGACTGTGTTTCTCCCTTC<br>5' Primer: (for DGGE) GC clamp-CCAGACTGTGTTTCTCCCTTC<br>3' Primer: (for DGGE and DNA sequencing) CACAAAGAAAGCCCTCCCCA |
| N-<u>ras</u> | 1 | 5' Primer: (for DGGE and DNA sequencing) GACTGAGTACAAACTGGTGG<br>3' Primer: (for DNA sequencing) GGGCCTCACCTCTATGGTG<br>3' Primer: (for DGGE) GC clamp-GGGCCTCACCTCTATGGTG |
| | 2 | 5' Primer: (for DNA sequencing) GGTGAAACCTGTTTGTTGGA<br>5' Primer: (for DGGE) GC clamp-GGTGAAACCTGTTTGTTGGA<br>3' Primer: (for DGGE and DNA sequencing) ATACACAGAGGAAGCCTTCG |
| H-<u>ras</u>-1 | 1 | 5' Primer: (for DGGE and DNA sequencing) CAGGCCCCTGAGGAGCGATG<br>3' Primer: (for DNA sequencing) TTCGTCCACAAAATGGTTCT<br>3' Primer: (for DGGE) GC clamp-TTCGTCCACAAAATGGTTCT |
| | 2 | 5' Primer: (for DGGE and DNA sequencing) TCCTGCAGGATTCCTACCGG<br>3' Primer: (for DNA sequencing) GGTTCACCTGTACTGGTGGA<br>3' Primer: (for DGGE) GC clamp-GGTTCACCTGTACTGGTGGA |

Sequence of the *GC clamp*:
5'-GCCGCCTGCAGCCCGCGCCCCCCGTGCCCCCGCCCCGCCGCCGGCCCGGCCGCC-3'

(1987). Two human ras pseudogenes, H-ras-2 and K-ras-1, have also been identified and mapped to the X chromosome and chromosome 6, respectively (Barbacid, *Ann. Rev. Biochem.*, 56, 779–827 (1987). The ras genes acquire their transformation-inducing properties mainly by single point mutations within their coding sequences, and in particular, by point mutations in the 12th, 13th or 61st codons in human tumors and tumor cell lines (Bos, *Cancer Research*, 49, 4682–4689 (1989); Barbacid, *Ann. Rev. Biochem.*, 56, 779–827 (1987). Accordingly, each cell line was examined to detect any departure from the H-ras-1, N-ras and K-ras-2 wild-type DNA sequence.

The examination of cell lines of the NCI panel was conducted by amplifying exons 1 and 2 of each ras gene by the polymerase chain reaction (PCR) using genomic DNA prepared from each cell line. The genomic DNA was isolated from the cell lines using a Cell Culture DNA Mini Kit (Qiagen, Inc., Chathsworth, Calif.) according to the recommendations of the manufacturer. The PCR reaction was carried out using a GeneAmp PCR Reagent Kit with Ampli-Taq DNA Polymerase and a GeneAmp PCR System 9600 (all from Perkin Elmer Co., Norwalk, Conn.), according to the recommendations of the manufacturer. The 5' and 3' primers (Genosys Biotechnologies, Inc., Woodlands, Tex.)

Also set forth in Table 7 are primers employed for denaturing gradient gel electrophoresis (DGGE), a sensitive technique that allows the detection of base changes in DNA sequences under conditions in which these changes could easily be missed by other detection techniques including DNA sequencing. DGGE calls for electrophoresis of DNA fragments through a polyacrylamide gel containing a chemical denaturant under conditions in which the DNA fragments partially melt, allowing sequence-dependent conformational changes to be detected as a variation in migration distance (Abrams et al., Meth. Enzymol., 212, 71–104 (1992).

The primers employed for DGGE contained at their 5'-ends a 54-base pair long, thermostable, GC-rich clamp sequence, or a "GC clamp". The GC-clamp has been demonstrated to modify the melting behavior of DNA fragments electrophoresed through denaturing polyacrylamide gels, such that even when present as only a minor fraction of the total DNA sample (e.g., 1 to 20%), point mutations within a DNA sequence can be detected.

The primers are also set forth in the Sequence Listing as follows: GC-clamp, SEQ ID NO:1; 5' primer for exon 1 of K-ras-2, SEQ ID NO:2; 3' primer for exon 1 of K-ras-2, SEQ ID NO:3; 3' primer (containing the GC-clamp) for exon 1 of K-ras-2, SEQ ID NO:4; 5' primer for exon 2 of K-ras-2, SEQ ID NO:5; 5' primer (containing the GC-clamp) for exon 2 of K-ras-2, SEQ ID NO:6; 3' primer for exon 2 of K-ras-2, SEQ ID NO:7; 5' primer for exon 1 of N-ras, SEQ ID NO:8; 3' primer for exon 1 of N-ras, SEQ ID NO:9; 3' primer (containing the GC-clamp) for exon 1 of N-ras, SEQ ID NO:10; 5' primer for exon 2 of N-ras, SEQ ID NO:11; 5' primer (containing the GC-clamp) for exon 2 of N-ras, SEQ ID NO:12; 3' primer for exon 2 of N-ras, SEQ ID NO:13; 5' primer for exon 1 of H-ras-1, SEQ ID NO:14; 3' primer for exon 1 of H-ras-1, SEQ ID NO:15; 3' primer (containing the GC-clamp) for exon 1 of H-ras-1, SEQ ID NO:16; 5' primer for exon 2 of H-ras-1, SEQ ID NO:17; 3' primer for exon 2 of H-ras-1, SEQ ID NO:18; 3' primer (containing the GC-clamp) for exon 2 of H-ras-1, SEQ ID NO:19.

Following amplification of the exons, the PCR products were separated by electrophoresis through a 6% polyacrylamide gel, and were recovered from the gel using the crush and soak method (Sambrook et al., *Molecular Cloning: A Laboratory Manual* 2nd Ed., (New York: Cold Spring Harbor Laboratory Press, 1989). The purified DNA fragments were then either directly sequenced or subjected to DGGE. DNA sequencing reactions were performed with the PRISM Ready Reaction DyeDeoxy Terminator Cycle Sequencing Kit (Applied Biosystems, Inc., Foster City, Calif.) according to the recommendations of the manufacturer, and the products were analyzed on an ABI 373A DNA Sequencer (Applied Biosystems, Inc.). DGGE was carried out as previously described (Abrams et al., *Meth. Enzymol.*, 212, 71–104 (1992) using a DGGE-2000 System (Marsh Biomedical Products, Inc., Rochester, New York).

Oncogenic mutations in ras genes (as determined by DGGE and direct DNA sequencing) present in the 60 cell lines which currently comprise the NCI panel and which were employed in the drug screen are presented in Table 8.

TABLE 3

Profile of rasmutations in 60 human tumor cell lines

| Cell Line | Mutations in rasgenes[a] |
|---|---|
| Leukemia | |
| CCRF-CEM | K codon 12: GAT(Asp) & N codon 12: GTT(Val) |
| HL-60(TB) | N codon 61: CTA(leu) |
| K-562 | WT |
| MOLT-4 | N codon 12: TGT(Cys) |
| RPMI-8226 | K codon 12: GCT(Ala) |
| SR | N codon 12: TGT(Cys) |
| Non-Small Cell Lung Cancer | |
| A549/ATCC | K codon 12: AGT(Ser) |
| EKVX | WT |
| HOP-62 | K codon 12: TGT(Cys) |
| HOP-92 | WT |
| NCI-H226 | WT |
| NCI-H23 | K codon 12: TGT(Cys) |
| NCI-H322M | WT |
| NCI-H460 | K codon 61: CAT(His) |
| NCI-HS22 | WT |
| Colon Cancer | |
| COLO-205 | WT |
| HCC-2998 | WT |
| HCT-116 | K codon 13: GAC(Asp) |
| HCT-15 | K codon 13: GAC(Asp) |
| HT-29 | WT |
| KM12 | WT |
| SW-620 | K codon 12: GTT(Val) |
| CNS Cancer | |
| SF-268 | WT |
| SF-295 | WT |
| SF-539 | WT |
| SNB-19 | WT |
| SNB-75 | WT |
| U251 | WT |
| Melanoma | |
| LOX IMVI | WT |
| M14 | WT |
| MALME-3M | WT |
| SK-MEL-2 | N codon 61: CGA(Arg) |
| SK-MEL-28 | WT |
| SK-MEL-5 | WT |
| UACC-257 | WT |
| UACC-62 | WT |
| Overian Cancer | |
| IGROV 1 | WT |
| OVCAR-3 | WT |
| OVCAR-4 | WT |
| OVCAR-5 | K codon 12: GTT(Val) |
| OVCAR-8 | WT |
| SK-OV-3 | WT |
| Renal Cancer | |
| 786-0 | WT |
| A498 | WT |
| ACHN | WT |
| CAKI-1 | WT |
| RXF-393 | WT |
| SN12C | K codon 13: GAC(Asp) |
| TK-10 | WT |
| UO-31 | WT |
| Prostate Cancer | |
| PC-3 | WT |
| DU-145 | WT |
| Breast Cancer | |
| MCF7 | WT |
| MCF7/ADR-RES | WT |
| MDA-MB-231/ATCC | K codon 13: GAC(Asp) |
| HS 578T | H codon 12: GAC(Asp) |
| MDA-MB-435 | WT |
| MDA-N | WT |
| BT-549 | WT |
| T-47D | WT |

[a]Mutations in rasgenes are shown: K, K-ras-2 gene; N, N-rasgene; H, H-ras-1 gene; WT, no mutation. The codon number, mutant sequence and amino acid by the mutant sequence are indicated for codons harboring oncogenic mutations.

Accordingly, it can be seen from Table S that gain of function ras mutations are obtained in all cell line members of the NCI panel of human transformed cells with the exception of the CNS (i.e., central nervous system) cancer cell lines. This method could similarly be employed to determine the status of other oncogenes present in transformed cells, including tumor suppressor genes.

EXAMPLE 2

Identifying drugs which selectively inhibit the growth of cancer cells containing activated ras genes In this Example, the relationship between the status of the ras gene present in a cell and sensitivity to a particular drug was determined.

Data on the activity of various drugs against NCI panel cell lines collected within the NCI database (as described in Monks et al., *J. Natl. Cancer Inst.*, 83, 757–766) was compared to the profile of ras mutations elucidated in Example 1. Two measures of statistics based on ranks were assessed: (1) the Pearson correlation coefficient (Snedecor et al., *Statistical Methods*, 7th Ed., 175–193 (Ames, IA: The Iowa State University Press, 1980); and (2) the Spearman correlation coefficient (Siegel, *Nonparametric Statistics for the Behavioral Sciences*, 195–213 (New York: McGraw-Hill Book Company, 1956).

These statistics were derived making use of a COMPARE computer program developed by Paull et al. to rank patterns of differential growth inhibition among the NCI panel cell lines (Paull et al., *J. Natl. Cancer Inst.*, 81, 1088–1092 (1989)). Subsequently the COMPARE program was used to predict the mechanism of action of a drug based on its pattern of activity against the NCI panel cell lines (Weinstein et al., *Science*, 258, 447–451 (1992). This would appear to be the first time the program has been used to screen for a correlation between drug sensitivity and genotype of cell lines of the NCI panel.

Using this approach, the profile of ras gene mutations was compared to the sensitivity patterns of 20,212 drugs for the 60 cell lines. The program was also used to test individual sets of tumor cell lines. Out of the 60 cell lines, the best correlation between the presence of an activated ras oncogene and sensitivity to a particular drug (at the $GI_{50}$, or 50% growth inhibition, level of effect) was observed for colon cancer and non-small cell lung cancer cells, as indicated by high Pearson and Spearman correlation coefficients. The ranking according to the Pearson correlation coefficient for colon cancer and non-small cell lung cancer cells is given in Table 9.

TABLE 9

Ranking According to the Pearson Correlation Coefficient (P)

| Ranking | NSC Number | PEARSON Correlation Coefficient (P) |
|---|---|---|
| 1 | 63878 | 0.907 |
| 2 | 656239 | 0.820 |
| 3 | 659687 | 0.816 |
| 4 | 284682 | 0.816 |
| 5 | 145668 | 0.815 |
| 6 | 641548 | 0.811 |
| 7 | 663337 | 0.806 |
| 8 | 642321 | 0.800 |
| 9 | 652173 | 0.800 |
| 10 | 638855 | 0.796 |
| 11 | 650931 | 0.793 |
| 12 | 632246 | 0.785 |
| 13 | 667730 | 0.784 |
| 14 | 303812 | 0.783 |
| 15 | 7364 | 0.781 |
| 16 | 648338 | 0.774 |
| 17 | 619029 | 0.770 |
| 18 | 642049 | 0.769 |
| 19 | 603335 | 0.768 |
| 20 | 352122 | 0.765 |
| 21 | 134679 | 0.761 |
| 22 | 654236 | 0.756 |

The ranking according to the Spearman correlation coefficient for colon cancer and non-small cell lung cancer cells is given in Table 10.

TABLE 10

Ranking according to the Spearman Correlation Coefficient (S)

| Ranking | NSC Number | SPEARMAN Correlation Coefficient (S) |
|---|---|---|
| 1 | 642321 | 0.878 |
| 2 | 63878 | 0.874 |
| 3 | 632246 | 0.869 |
| 4 | 660027 | 0.869 |
| 5 | 660028 | 0.869 |
| 6 | 667730 | 0.863 |
| 7 | 663337 | 0.862 |
| 8 | 638855 | 0.861 |
| 9 | 641548 | 0.835 |
| 10 | 141540 | 0.834 |
| 11 | 284682 | 0.834 |
| 12 | 652173 | 0.834 |
| 13 | 659687 | 0.834 |
| 14 | 615291 | 0.821 |
| 15 | 134679 | 0.806 |
| 16 | 145668 | 0.806 |
| 17 | 317003 | 0.806 |
| 18 | 375575 | 0.806 |
| 19 | 650362 | 0.806 |
| 20 | 652565 | 0.788 |
| 21 | 303812 | 0.787 |
| 22 | 631522 | 0.787 |
| 23 | 656239 | 0.787 |
| 24 | 656240 | 0.787 |

The chemical structures of the drugs contained in Tables 9 and 10 are presented in Table 6. The maximum test concentration employed for determining drug sensitivity at which a correlation was found, as well as the number of times sensitivity was tested, and the number of strains employed for testing are presented in Table 11.

TABLE 11

Test Conditions for Drugs

| NSC Number | Maximum Test Conc. (μM) | Times Tested | N | Chemical Name |
|---|---|---|---|---|
| 7364 | 100 | 3 | 16 | Methodichlorophen |
| 63878 | 100 | 2 | 16 | Cytosine Arabinoside |
| 134679 | 100 | 3 | 16 | Bizelesin |
| 141540 | 25 | 7 | 16 | Epipodophyllotoxin VP-16213 (VP-16) |
| 145668 | 1000 | 15 | 16 | Cyclocytidine |
| 284682 | 10 | 4 | 16 | 3'-Hydroxydaunorubicin |
| 303812 | 100 | 2 | 15 | Aphidicolin Glycinate |
| 317003 | 100 | 3 | 16 | 9H-Thioxanthen-9-one, 1-[[2-(dimethylamino)ethyl]amino]-7-hydroxy-4-methyl-, monohydriodide |
| 352122 | 1 | 4 | 16 | Trimetrexate |
| 375575 | 500 | 13 | 16 | Cyclopentenylcytosine |
| 603335 | 100 | 4 | 16 | 2-Pyridone, 3-Chloro-4-hydroxy-1-β-d-ribofuranosyl |
| 615291 | 0.1 | 1 | 12 | a CC-1065 Analog |
| 619029 | 1000 | 1 | 15 | |
| 631522 | 100 | 1 | 15 | |
| 632246 | 100 | 1 | 12 | |
| 638955 | 100 | 3 | 16 | Carbazilquinone |
| 641548 | 100 | 1 | 15 | Betuletol |
| 642049 | 100 | 3 | 16 | |
| 642321 | 1 | 1 | 14 | |
| 649338 | 100 | 1 | 8 | |
| 650362 | 100 | 2 | 16 | |
| 650931 | 100 | 1 | 15 | 2'-Bromo-4'-epi-daunorubicin |
| 652173 | 100 | 2 | 16 | |
| 652565 | 100 | 1 | 14 | |
| 654236 | 100 | 4 | 16 | |
| 656239 | 100 | 2 | 15 | |
| 656240 | 100 | 2 | 15 | |
| 659687 | 100 | 2 | 16 | |
| 660027 | 25 | 1 | 12 | |
| 660028 | 100 | 1 | 12 | |
| 663337 | 10 | 1 | 15 | |
| 667730 | 100 | 1 | 12 | |

The importance of the ras gene in lung and cancer cells as reflected in the statistical rankings obtained for these cell types is consistent with previous observations of a high incidence of ras gene mutations in cancers of the colon and lung (Bos, *Cancer Res.*, 49, 4682–4689 (1989; Barbacid, *Ann. Rev. Biochem.*, 56, 779–827 (1987)). Further, such data confirm that specific oncogenes can render cells sensitive to specific types of antineoplastic drugs.

It is possible that gain of function mutations in ras oncogenes may similarly render other types of cancer cells sensitive to these drugs. For instance, a high incidence of ras mutations is found in cancers of the pancreas, thyroid and liver, and in myeloid leukemia (Bos, *Cancer Res.*, 49, 4682–4689 (1989)), which might suggest that these types of cancer cells would be sensitive to the drugs in Table 6. Unfortunately, such possibilities cannot be tested using the current NCI panel of cell lines due to the ras genotypes of these lines. For instance, the CNS cancer cell lines do not comprise any ras mutants, and the melanoma, ovarian cancer, renal cancer, prostrate cancer and breast cancer cell lines comprise too few ras mutant cell lines to allow ranking of variables and calculation of correlation coefficients. The opposite problem manifests with the leukemia cell lines, where the overabundance of the mutant ras genotype in the sample of cell lines prevents statistical calculations from being derived. It is possible, however, that inclusion of different cell lines in the NCI panel in the future, as well as use of the approach in the following Example, will allow the possibility of the identified drugs having a selective inhibitory effect on these other types of cancer cells in which the ras gene may be important for neoplasia to be tested.

Accordingly, these studies identify an important new way to identify drugs which selectively target cancer cells containing an activated oncogene. The studies also point out the ability of particular antineoplastic drugs to target lung and colon cancer cells containing an activated ras oncogene. The approach outlined in this Example can also be used to identify drugs which selectively inhibit growth of cells containing activated oncogenes other than ras. Moreover, the approach can be modified to take into consideration the ramifications of the multi-drug resistant phenotype (i.e., MDR$^+$, which renders a cell resistant to numerous agents) on the statistical ranking, such as, for example, excluding cell lines exhibiting this phenotype from the ranking.

EXAMPLE 3

Use of other cell lines to identify drugs which selectively inhibit the growth of cancer cells containing activated oncogenes This Example outlines the method of screening for drugs which selectively inhibit the growth of particular types of cancer cells which cannot be tested using the approach outlined in Example 2.

In the method of the present invention, cell lines other than those comprising the NIH panel can also be employed in drug sensitivity testing. Moreover, new cell lines containing activated oncogenes can be generated from transformed cell lines and screened.

In this Example, cell lines were cultured in vitro using standard tissue culture methodology (e.g., use of sterile culture conditions and well known media and reagents, maintenance of cultures in an enriched $CO_2$ atmosphere or use of appropriate media allowing growth under atmospheric conditions, etc.). Six cell lines (all obtained from American Type Culture Collection, Rockville, Md.) were employed: a parental non-tumorigenic cell line derived from human osteosarcoma, HOS; a tumorigenic cell line derived from HOS cells transformed by v-K-ras, KHOS-NP; two non-tumorigenic revertant derivatives of the KNOS-NP line, KHOS-240S and KHOS-312H; a transformed derivative of the HOS cell line obtained by exposure of the HOS cells to a carcinogen MNNG and from which the trp-met oncogene was cloned, MNNG/HOS; and a transformed cell line derived from HOS cells treated with the carcinogen DMBA, DMBA/HOS.

Initially, twenty antineoplastic drugs were tested against these cell lines using a previously outlined approach (Monks et al., *J. Natl. Cancer Inst.*, 83, 757–766). Exposure of the six cell lines to the glycopeptide antibiotic bleomycin indicated an on average two-fold greater sensitivity of the KHOS-NP cell line to all drug concentrations tested as compared with the parental HOS line. Bleomycin has been shown to bind DNA, inducing DNA single strand- and double strand-breaks, and to act within the $G_2/M$ phase of the cell cycle (Dorr, *Semin. Oncol.*, 19(Suppl. 5), 3–8 (1992).

Similarly, exposure of the six cell lines to the nonsteroidal antiestrogen tamoxifen indicated a greater sensitivity of the KHOS-NP cell line to as compared with the parental HOS line. The cellular response pattern suggested a threshold for a drug concentration effective against these cells. Tamoxifen has been reported to inhibit protein kinase C in an intracellular transduction pathway (Suet al., *Biochem. Pharmacol.*, 34, 3649–3653 (1985); Horgan et al., *Biochem. Pharmacol.*, 35, 4463–4465 (1986)). The other four cell lines demonstrated intermediate sensitivity to bleomycin and tamoxifen as compared to the parental HOS cells.

These results indicate that the KHOS-NP cells show sensitivity to two different drugs that work on different stages of the cell cycle, relative to the parental HOS cells. Moreover, the results confirm that cell lines other than those comprising the NCI panel can be employed to identify drugs which selectively inhibit the growth of cancer cells containing activated oncogenes.

This approach can similarly be employed with other established cell lines. Moreover, cell lines containing particular oncogenes can be generated by transfection of established cell lines with the appropriate genomic or cDNA sequences.

EXAMPLE 4

Characterization of drug nature and action

The drugs identified in Example 2 as being capable of selectively inhibiting the growth of colon and lung cancer cells containing an activated ras oncogene were further characterized in this Example.

The classes and putative modes of action for some of the antineoplastic drugs identified in Table 6 are given in Table 12. The drugs appear to fall into four main classes based on their proposed mechanism of action: pyrimidine analogs and pyrimidine biosynthesis inhibitors; antifolates; topoisomerase II inhibitors; and alkylating agents.

TABLE 12

Classes and Putative Modes of Action for Antineoplastic Drugs

| NSC Number | Chemical Name |
| --- | --- |
| Pyrimidine analogs & Pyrimidine Biosynthesis Inhibitors | |
| 63878 | Cytosine Arabinoside |
| 663337 | |
| 145668 | Cyclocytidine |
| 375575 | Cyclopentenylcytosine |
| 652565 | |
| 603335 | 2-Pyridinone, 3-chloro-4-hydroxy-1-β-D-ribofuranosyl |
| 303812 | Aphidicolin glycinate |
| 631522 | |
| Antifolates | |
| 7364 | Methodichlorophen |
| 352122 | Trimetrexate |
| Topoisomerase II Inhibitors | |
| 284682 | 3'-Hydroxydaunorubicin |
| 650931 | 2'-Bromo-4'-epi-daunorubicin |
| 141540 | Epipodophyllotoxin VP-16213 (VP-16) |
| 317003 | 9H-Thioxanthen-9-one, 1-[[2-(dimethylamino)ethyl]amino]-7-hydroxy-4-methyl-, monohydriodide |
| 641548 | Betuletol |
| 660027 | |
| 660028 | |
| 659687 | |
| 650362 | |
| Alkylating agents | |
| 638855 | Carbazilquinone |
| 134679 | Bizelesin |
| 615291 | a CC-1065 analog |
| 619029 | |

Furthermore, the characterization of some of these antineoplastic drugs as either upstream or downstream reacting compounds based on their known or putative targets in the cell cycle is indicated in Table 13.

TABLE 13

Selected Antineoplastic Agents and Their Possible Cellular Targets

| $G_1$ + S-phase (Upstream) | M-phase (Downstream) |
| --- | --- |
| DNA Synthesis | Topoisomerase II Inhibitor |
| Cytosine Arabinoside | 3'-Hydroxydaunorubicin |
| Cyclocytidine | 2'-Bromo-4'-epi-daunorubicin |
| Cyclopentenylcytosine | VP-16 |
| 2-Pyridinone, 3-Chloro-4-hydroxy,-1-β-d-ribofuranosyl | 9H-thioxanthen-9-one,1-[[2-(dimethylamino)ethyl] amino]-7-hydroxy-4-methyl-, monohydriodide |
| Aphidicolin Glycinate | Betuletol |
| Methodichlorophen | |
| Trimetrexate | |
| DNA Alkylation | |
| Carbazilquinine | |
| Bizelesin | |

These results confirm that the drugs identified as capable of selectively targeting lung and colon cancer cells containing an activated ras oncogene can conceivably be employed in the treatment of cancer, as set forth in the following Example.

EXAMPLE 5

Method of using the drugs identified in the present screen to selectively inhibit the growth of colon and lung cancer cells This Example outlines methods of using the drugs identified in Example 2 as being capable of selectively inhibiting the growth of colon and lung cancer cells containing an activated oncogene.

The drugs identified in Table 6 can be employed in a method of selectively inhibiting the growth of lung and colon cancer wherein such cancer comprises an activated ras oncogene. While any dose which results in 50% growth inhibition (as measured by a variety of parameters including increase in tumor size or mass, rate of growth in vivo or of a biopsied sample in vitro, etc.) can be employed, the preferred dose of each drug for inhibition is that indicated in Table 11.

The characterization of the drugs as either upstream or downstream reacting compounds further suggests that the drugs can be employed in treatment in synergistic combinations. Namely, by employing a first drug which inhibits cancer cell growth by exerting its primary effect on the mammalian cell cycle prior to or during S-phase, and a second drug which inhibits cancer cell growth by exerting its primary effect on the cell cycle after S-phase and prior to or during M-phase. Such synergistic drugs can be employed concurrently, as for instance, in the same pharmaceutical composition, or can be administered in separate pharmaceutical compositions. Regardless of how such drugs are administered, it is preferable that administration be conducted such that the drugs exert their respective effects upon the cell cycle at the same time. Moreover, it may be necessary to reduce the dose of a particular antineoplastic agent when synergy with another antineoplastic drug is obtained. This is a desirable situation in that toxicity to non-cancerous cells should be reduced. In these types of situations, the dose should be reduced to the lowest level at which a therapeutic response is observed, and at which toxic effects of the drug are minimized.

EXAMPLE 6

Use of the method of the present invention for treating cancer in a patient

This Example outlines the use of the method of the present invention in the treatment of cancer on a case-by-case basis.

The present invention points out a previously unrecognized relationship between the presence of an activated oncogene in a particular type of cancer cell, and sensitivity of that cell to particular antineoplastic agents. Thus, the method can theoretically be employed to design anticancer therapy for a particular patient. Namely, a cancer cell can be isolated from a patient and tested using the methods outlined herein for the presence of an activated oncogene such as the ras oncogene. If the cancer cell comprises an activated oncogene known to render that type of cancer cell sensitive to a particular anti-neoplastic agent, then the cancer can be treated by administering a drug known to selectively inhibit the growth of that particular type of cancer cell which comprises an activated oncogene, such as aras oncogene.

This method of treatment would present a major advance over standard methods of treatment, in which drug effectiveness in vivo is determined on an empirical basis, and no convenient means is available for assessing a priori whether a given drug will likely be effective against a particular type of cancer.

Moreover, the method of designing anticancer therapy for a particular type of cancer in a patient can optimally be coupled with the method of identification of drugs which selectively inhibit the growth of a particular type of cancer cell comprising an activated oncogene such as aras oncogene, as set forth in Examples 1–3. Using this novel method of identification of drugs capable of targeting particular types of cancer, it is envisioned that a computer database (analogous to the NCI database compiling drug sensitivity data) will be derived wherein considerable data is collected linking the presence of different activated oncogenes in particular cell types to sensitivity to certain antineoplastic drugs. It is anticipated that this database will serve as a valuable storehouse of information in designing anticancer treatment for a particular patient. All of the references cited herein, including patents, patent applications, GenBank® Data Bank listings, and publications are hereby incorporated in their entireties by reference.

While this invention has been described with an emphasis upon a preferred embodiment, it will be obvious to those of ordinary skill in the art that variations in the preferred methods may be used, including variations due to improvements in the art, and that it is intended that the invention be practiced otherwise than as specifically described herein, to encompass these variations. Accordingly, this invention includes all modifications encompassed within the spirit and scope of the invention as defined by the following claims.

What is claimed is:

1. A method of identifying a drug which selectively inhibits the growth of a particular type of cancer cell, which method comprises:

(a) contacting with said drug at least two cancer cells derived from the same type of biological material, wherein said cancer cells differ as to the presence of a particular DNA sequence that was acquired in vivo, (b) measuring the effect of said drug on the growth of said cancer cells, and (c) determining whether there is a correlation between the effect of said drug on said cancer cells and the presence or absence of said DNA sequence in said cancer cells.

2. The method of claim 1, wherein said DNA sequence comprises an oncogenic tumor suppressor gene.

3. The method of claim 1, wherein said DNA sequence comprises an activated oncogene.

4. The method of claim 3, wherein said DNA sequence comprises an activated ras oncogene.

5. The method of claim 4, wherein said ras oncogene is K-ras-2.

6. The method of claim 5, wherein said K-ras-2 oncogene has been activated by a mutation in the 12th, 13th or 61st codon.

7. The method of claim 1, wherein said cancer cells are non-small cell lung cancer cells and wherein said DNA sequence comprises an activated oncogene or an oncogenic tumor suppressor gene.

8. The method of claim 7, wherein said DNA sequence comprises an activated oncogene.

9. The method of claim 8, wherein said DNA sequence comprises an activated ras oncogene.

10. The method of claim 9, wherein said ras oncogene is K-ras-2.

11. The method of claim 10, wherein said K-ras-2 oncogene has been activated by a mutation in the 12th, 13th or 61st codon.

12. The method of claim 1, wherein said cancer cell are colon cancer cells and wherein said DNA sequence comprises an activated oncogene or an oncogenic tumor suppressor gene.

13. The method of claim 12, wherein said DNA sequence comprises an activated oncogene.

14. The method of claim 13, wherein said DNA sequence comprises an activated ras oncogene.

15. The method of claim 14, wherein said ras oncogene is K-ras-2.

16. The method of claim 15, wherein said K-ras-2 oncogene has been activated by a mutation in the 12th, 13th or 61st codon.

17. The method of claim 1, wherein said cancer cells derived from the same type of biological material are obtained from different patients.

18. The method of claim 1, wherein said method comprises contacting with said drug more than two cancer cells derived from the same type of biological material.

19. The method of claim 1, wherein said cancer cells derived from the same type of biological material are obtained from the same patient.

* * * * *